(12) United States Patent
Mikoshiba et al.

(10) Patent No.: US 6,492,100 B2
(45) Date of Patent: Dec. 10, 2002

(54) SILVER HALIDE COLOR PHOTOGRAPHIC LIGHTSENSITIVE MATERIAL AND COMPOUND USED THEREIN

(75) Inventors: Hisashi Mikoshiba, Minami-Ashigara (JP); Yoshio Shimura, Minami-Ashigara (JP); Naoto Matsuda, Minami-Ashigara (JP); Hiroshi Fukuzawa, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/923,456

(22) Filed: Aug. 8, 2001

(65) Prior Publication Data

US 2002/0051948 A1 May 2, 2002

(30) Foreign Application Priority Data

Aug. 14, 2000 (JP) .................................. 2000-245812
Jan. 29, 2001 (JP) .................................. 2001-020183

(51) Int. Cl.$^7$ .................................. G03C 1/08
(52) U.S. Cl. ................ 430/558; 430/387; 430/378; 430/379
(58) Field of Search ................ 430/453, 558, 430/378, 379, 387

(56) References Cited

U.S. PATENT DOCUMENTS

| | | | |
|---|---|---|---|
| 4,835,094 A | | 5/1989 | Wolff et al. |
| 5,183,728 A | | 2/1993 | Romanet et al. |
| 5,256,529 A | * | 10/1993 | Romanet et al. ............ 430/558 |
| 5,302,496 A | | 4/1994 | Romanet et al. |
| 5,576,150 A | * | 11/1996 | Tang et al. .................. 430/558 |
| 5,698,386 A | * | 12/1997 | Tang et al. .................. 430/558 |
| 5,925,503 A | * | 7/1999 | Harder et al. ................ 430/558 |
| 5,985,533 A | * | 11/1999 | Romanet et al. ............ 430/558 |

FOREIGN PATENT DOCUMENTS

| | | | |
|---|---|---|---|
| EP | 512304 A1 | | 11/1992 |
| JP | 6-186707 | * | 7/1994 |

\* cited by examiner

*Primary Examiner*—Geraldine Letscher
(74) *Attorney, Agent, or Firm*—Birch, Stewart, Kolasch & Birch LLP

(57) ABSTRACT

A silver halide color photographic lightsensitive material comprising at least one photosensitive silver halide emulsion layer on a support, wherein the emulsion layer contains a magenta coupler represented by formula (M-1) below:

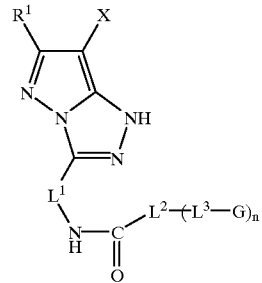

(M-1)

wherein $R^1$ represents a substituted or nonsubstituted alkyl group, each of $L^1$ and $L^2$ independently represents a substituted or nonsubstituted alkylene group, or substituted or nonsubstituted arylene group, in —$L^3$—G, $L^3$ represents —NH—$SO_2$— or —$SO_2$—NH—CO— (in these representations, bonding direction is not defined) and G represents a substituted or nonsubstituted alkyl group or substituted or nonsubstituted aryl group, alternatively —$L^3$—G represents —COOH or OH, X represents a hydrogen atom or a group which splits off when coupling with an oxidized form of a developing agent, n represents 1 or 2, when $L^2$ is an alkylene group, or n represents an integer from 1 to 5, when $L^2$ is an arylene group, and a plurality of —$L^3$—G's can be the same or different, when n is 2 or more.

19 Claims, No Drawings

SILVER HALIDE COLOR PHOTOGRAPHIC LIGHTSENSITIVE MATERIAL AND COMPOUND USED THEREIN

CROSS-REFERENCE TO RELATED APPLICATIONS

This application is based upon and claims the benefit of priority from the prior Japanese Patent Applications No. 2000-245812, filed Aug. 14, 2000; and No. 2001-020183, filed Jan. 29, 2001, the entire contents of both of which are incorporated herein by reference.

BACKGROUND OF THE INVENTION

1. Field of the Invention

The present invention relates to a silver halide color photographic lightsensitive material and a novel color coupler compound used therein.

2. Description of the Related Art

Many photographic couplers are used as they are dispersed in high-boiling organic solvents such as phosphoric ester and phthalic ester. On the other hand, lightsensitive materials for photographing are required to be thin in order to improve the sharpness. Therefore, couplers used in lightsensitive materials for photographing are dispersed by emulsification by using no high-boiling organic solvents (so-called oilless dispersion) or by using only slight amounts of high-boiling organic solvents. Compared to a case in which high-boiling organic solvents are used, the color forming efficiency lowers, and the absorption spectrum broadens.

Also, silver halide color photographic lightsensitive materials are strongly required to have faithful color reproducibility in addition to high sensitivity, high sharpness, and high granularity.

In the field of silver halide color photographic lightsensitive materials, a 1-phenyl-5-pyrazolone coupler has been conventionally widely used as a magenta coupler. On the other hand, some pyrazoloazole-based couplers having little side absorption and good hue, which are favored as image forming dyes, have been put into practical use.

Pyrazolotriazole magenta couplers are excellent compounds in that they have good hue. However, when introduced into lightsensitive materials, they pose various problems such as low color forming efficiency, low resistance against processing variations, and low color image storage stability.

In particular, a 4-equivalent pyrazolotriazole magenta coupler which couples with an oxidized form of an aromatic primary amine developing agent in the position of hydrogen atom substitution has low color forming efficiency, although it has high granularity, and has a large degree of yellow coloration which occurs by the lapse of time after development. On the other hand, a 2-equivalent coupler whose coupling position is substituted by a split-off group (e.g., a halogen atom) except for a hydrogen atom generates a color with a smaller silver amount than a 4-equivalent coupler. Although this 2-equivalent coupler does not easily cause yellow coloration, the granularity lowers, and this degrades the image quality.

To solve these problems, couplers in which substituents on pyrazoloazole rings are variously improved have been proposed. For example, U.S. Pat. No. 4,882,266 and European Patent Publication No. 183,445 disclosed improvements of the light fastness of a color image by couplers in which the bulkiness of a 6-position substituent is increased. Jpn. Pat. Appln. KOKAI Publication No. (hereinafter referred to as JP-A-)1-102557 disclosed improvements of the color forming efficiency in oilless processing by couplers in which carboxylic acid is introduced as a dissociation group into coupler molecules. JP-A-5-150419 describes a coupler having a sulfonamide bond. JP-A-63-291058 also describes a coupler similar to the present invention. Unfortunately, when the present inventors attempted to apply these techniques, they newly found that improvements of yellow coloration and color image storage stability by these techniques during the lapse of time after processing were still unsatisfactory. Also, they newly found that the couplers increased the cost and deteriorated the crystallinity and hence could not be used in industrial applications. Furthermore, they newly found that the sensitivity decreased when the couplers were retained before coating after they were mixed in color-sensitized silver halide emulsions.

Most pyrazoloazole-based couplers currently put into practical use are 2-equivalent couplers having a split-off group except for a hydrogen atom in a portion where these couplers react with an oxidized form of a color developing agent. Color reversal photographic lightsensitive materials are subjected to first development, reversal processing, and color development in this order. 2-equivalent couplers have an essential problem that since they have high color forming efficiency per mol of silver, they decrease the sensitivity compared to 4-equivalent couplers. Therefore, when pyrazoloazole magenta couplers are to be applied to color reversal photographic lightsensitive materials, 4-equivalent couplers are preferred in respect of sensitivity. From this viewpoint, the couplers described in JP-A's-5-150419 and 63-291058 are unfavorable because they are primarily 2-equivalent couplers. Applications of 4-equivalent pyrazoloazole magenta couplers to color reversal photographic lightsensitive materials are described in, e.g., JP-A's-5-100382 and 63-153548. However, these techniques have not solved the above-mentioned problem of yellow coloration caused by the lapse of time after processing. In addition, the problem of the absorption spectrum of a generated dye in oilless dispersion remains unsolved.

BRIEF SUMMARY OF THE INVENTION

It is the first object of the present invention to provide a silver halide color photographic lightsensitive material which has high color reproducibility and high image stability and produces stains little. It is the second object of the present invention to provide a coupler which achieves high color forming efficiency even when the use amount of a high-boiling organic solvent is reduced. It is the third object of the present invention to provide a novel pyrazolotriazole-based compound which can be manufactured at low cost and has high manufacturing suitability. It is the fourth object of the present invention to provide a silver halide color photographic lightsensitive material which lowers the sensitivity little when stored and changes photographic properties little by variations in processing compositions.

The present inventors made extensive studies on the structure and photographic properties of pyrazolotriazole couplers. As a consequence, the present inventors have found couplers solving the above problems and thereby completed the present invention.

That is, the objects of the present invention were achieved by the following lightsensitive material and compound.

(1) A silver halide color photographic lightsensitive material comprising at least one photosensitive silver halide emulsion layer on a support, wherein the emulsion layer contains a magenta coupler represented by formula (M-1) below:

(M-1)

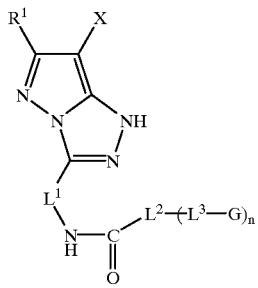

wherein $R^1$ represents a substituted or nonsubstituted alkyl group; each of $L^1$ and $L^2$ independently represents a substituted or nonsubstituted alkylene group, or substituted or nonsubstituted arylene group; in —$L^3$— G, $L^3$ represents —NH—$SO_2$— or —$SO_2$—NH—CO— (in these representations, bonding direction is not defined) and G represents a substituted or nonsubstituted alkyl group or substituted or nonsubstituted aryl group, alternatively —$L^3$—G represents —COOH or OH; X represents a hydrogen atom or a group which splits off when coupling with an oxidized form of a developing agent; n represents 1 or 2, when $L^2$ is an alkylene group, or n represents an integer from 1 to 5, when $L^2$ is an arylene group; and a plurality of —$L^3$—G's can be the same or different, when n is 2 or more.

(2) A silver halide color photographic lightsensitive material comprising at least one photosensitive silver halide emulsion layer on a support, wherein the emulsion layer contains a magenta coupler represented by formula (M-2) below:

(M-2)

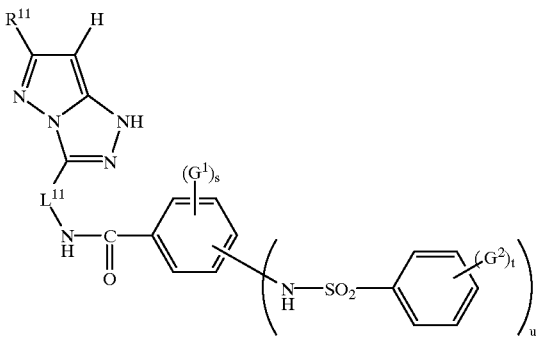

wherein $R^{11}$ represents a 1- to 6-carbon nonsubstituted alkyl group; $L^{11}$ represents a 1 to 6-carbon nonsubstituted alkylene group; each of $G^1$ and $G^2$ independently represents a substituted or nonsubstituted alkyl group, substituted or nonsubstituted alkoxy group, substituted or nonsubstituted aryloxy group, halogen atom, substituted or nonsubstituted acylamino group, substituted or nonsubstituted alkoxycarbonyl group, or substituted or nonsubstituted aminocarbonyl group; s represents an integer from 0 to 4; t represents an integer from 0 to 5; u represents 1 or 2; the sum of s and u does not exceed 5; and the value of pKa of —$NHSO_2$— between the two phenyl groups at 25° C. in a solution of THF/$H_2O$= 6/4 is 12 or less.

(3) A compound represented by formula (M-3) below:

(M-3)

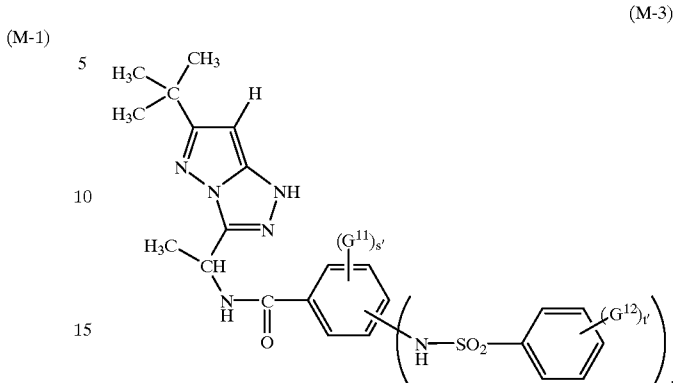

wherein each of $G^{11}$ and $G^{12}$ independently represents a 1- to 30-carbon, substituted or nonsubstituted alkyl group, 1- to 30-carbon, substituted or nonsubstituted alkoxy group, 6- to 30-carbon, substituted or nonsubstituted aryloxy group, halogen atom, 1- to 30-carbon, substituted or nonsubstituted acylamino group, 2- to 30-carbon, substituted or nonsubstituted alkoxycarbonyl group, or 1- to 30-carbon, substituted or nonsubstituted aminocarbonyl group; s' represents an integer from 0 to 4; t' represents an integer from 0 to 5; u' represents 1 or 2; and the sum of s' and u' does not exceed 5.

A magenta coupler of the present invention is a novel compound and shows very high performance even in a color negative photographic lightsensitive material. Also, a magenta coupler of the present invention is useful not only as a coupler for a silver halide photographic lightsensitive material but also as a material intermediate of medicines and agricultural chemicals.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

The present invention will be described in detail below. In this specification, "nonsubstituted alkyl groups" mean straight-chain, branched, and cyclic alkyl groups, e.g., an n-butyl group, 2-ethylhexyl group, t-butyl group, and cyclohexyl group. "Substituted alkyl" will be described in detail below.

The present invention provides a silver halide color photographic lightsensitive material comprising at least one silver halide emulsion layer on a support, wherein at least one of the emulsion layers contains a magenta coupler represented by formula (M-1) below.

(M-1)

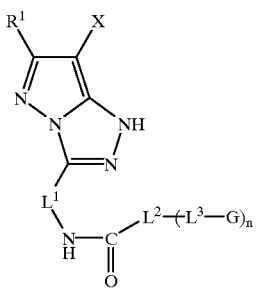

In formula (M-1), $R^1$ represents a substituted or nonsubstituted alkyl group. $R^1$ is preferably a 1- to 30-carbon, substituted or nonsubstituted alkyl group. Examples of a substituent for substituting this alkyl group are an aryl group, heterocyclic group, acyl group, acyloxy group, acylamino group, alkoxy group, aryloxy group, heterocyclic oxy group, alkoxycarbonyl group, aryloxycarbonyl group, a heterocyclic oxycarbonyl group, alkylcarbamoyl group, arylcarbamoyl group, alkylsulfonyl group, arylsulfonyl group, alkylsulfamoyl group, arylsulfamoyl group, alkylsulfonylamino group, amino group (including an anilino group), alkylsulfinyl group, arylsulfinyl group, alkylthio group, arylthio group, mercapto group, hydroxyl group, cyano group, nitro group, hydroxyamino group, carboxyl group, sulfo group, and halogen atom. Practical examples are those enumerated as substituents for substituting $L^1$ and $L^2$ to be described later. Practical examples of the heterocyclic oxycarbonyl group, alkylcarbamoyl group, arylcarbamoyl group, alkylsulfamoyl group, and arylsulfamoyl group are furyloxycarbonyl, methylcarbamoyl, phenylcarbamoyl, dimethylsulfamoyl, and phenylsulfamoyl, respectively. Examples of $R^1$ are methyl, ethyl, n-propyl, isopropyl, t-butyl, n-octyl, eicosyl, 2-chloroethyl, 2-cyanoethyl, and 2-ethylhexyl. $R^1$ is particularly preferably an alkyl group not containing a hetero atom, i.e., an alkyl group made up of only carbon atoms and hydrogen atoms, and more preferably a 1- to 10-carbon, straight-chain, branched, or cyclic, nonsubstituted alkyl group. $R^1$ is more preferably a 1- to 6-carbon, nonsubstituted alkyl group, further preferably isopropyl or t-butyl, and most preferably t-butyl.

In formula (M-1), $L^1$ represents a substituted or nonsubstituted alkylene group or substituted or nonsubstituted arylene group. Examples of a substituent when this alkylene group or arylene group is substituted are a halogen atom, alkyl group (including a cycloalkyl group), aryl group, heterocyclic group, cyano group, hydroxyl group, nitro group, carboxyl group, alkoxy group, aryloxy group, silyloxy group, heterocyclic oxy group, acyloxy group, carbamoyloxy group, alkoxycarbonyloxy group, aryloxycarbonyloxy group, amino group (including an anilino group), acylamino group, aminocarbonylamino group, alkoxycarbonylamino group, aryloxycarbonylamino group, sulfamoylamino group, alkylsulfonylamino and arylsulfonylamino groups, mercapto group, alkylthio group, arylthio group, heterocyclic thio group, sulfamoyl group, sulfo group, alkylsulfinyl and arylsulfinyl groups, alkylsulfonyl and arylsulfonyl groups, acyl group, aryloxycarbonyl group, alkoxycarbonyl group, carbamoyl group, arylazo and heterocyclic azo groups, imide group, phosphino group, phosphinyl group, phosphinyloxy group, phosphinylamino group, and silyl group.

More specifically, examples of the substituent are as follows:

a halogen atom (e.g., a chlorine atom, bromine atom, and iodine atom);

alkyl group {a straight-chain, branched, or cyclic alkyl group, more specifically, a substituted or nonsubstituted alkyl group having preferably 1 to 40 carbon atoms (e.g., methyl, ethyl, n-propyl, isopropyl, t-butyl, n-octyl, n-octadecyl, eicosyl, 2-chloroethyl, 2-cyanoethyl, and 2-ethylhexyl), substituted or nonsubstituted cycloalkyl group having preferably 3 to 40 carbon atoms (e.g., cyclohexyl, cyclopentyl, and 4-n-dodecylcyclohexyl), bicycloalkyl group (preferably a 5- to 30-carbon, substituted or nonsubstituted bicycloalkyl group, i.e., a monovalent group obtained by removing one hydrogen atom from 5- to 30-carbon bicycloalkane, e.g., bicyclo[1,2,2]heptane-2-yl and bicyclo[2,2,2]octane-3-yl), and group of tricyclo structure having a larger number of ring structures. An alkyl group in substituents to be explained below (e.g., an alkyl group in an alkylthio group) also represents an alkyl group having this concept};

aryl group (preferably a 6- to 50-carbon, substituted or nonsubstituted aryl group, e.g., phenyl, p-tolyl, naphthyl, m-chlorophenyl, o-hexadekanoylaminophenyl, and p-tert-octylphenyl);

heterocyclic group {preferably a monovalent group obtained by removing one hydrogen atom from a 5- or 6-membered, substituted or nonsubstituted, aromatic or non-aromatic heterocyclic compound, an aromatic ring such as benzene being able to be condensed, and more preferably a 3- to 30-carbon, 5- or 6-membered aromatic heterocyclic group. A heterocyclic ring preferably has at least one nitrogen atom, at least one oxygen atom, or at least one sulfur atom, and more preferably has at least one nitrogen atom. Examples of the heterocyclic ring are 2-furyl, 2-thienyl, 2-pyrimidinyl, and 2-benzothiazolyl. A heterocyclic group in substituents to be explained below (e.g., a heterocyclic group in a heterocyclic oxy group) also represents a heterocyclic group having this concept};

cyano group;

hydroxyl group;

nitro group;

carboxyl group;

alkoxy group (preferably a 1- to 30-carbon, substituted or nonsubstituted alkoxy group, e.g., methoxy, ethoxy, isopropoxy, t-butoxy, n-octyloxy, and 2-methoxyethoxy);

aryloxy group (preferably a 6- to 30-carbon, substituted or nonsubstituted aryloxy group, e.g., phenoxy, 2-methylphenoxy, 4-t-butylphenoxy, 3-nitrophenoxy, and 2-tetradecanoylaminophenoxy);

silyloxy group (preferably a 3- to 20-carbon silyloxy group, e.g., trimethylsilyloxy and t-butyldimethylsilyloxy);

heterocyclic oxy group (preferably a 2- to 30-carbon, substituted or nonsubstituted heterocyclic oxy group, e.g., 1-phenyltetrazole-5-oxy and 2-tetrahydropyranyloxy);

acyloxy group (preferably a formyloxy group, 2- to 30-carbon, substituted or nonsubstituted alkylcarbonyloxy group, and 7- to 30-carbon, substituted or nonsubstituted arylcarbonyloxy group, e.g., formyloxy, acetyloxy, pivaloyloxy, stearoyloxy, benzoyloxy, and p-methoxyphenylcarbonyloxy);

carbamoyloxy group (preferably a 1- to 30-carbon, substituted or nonsubstituted carbamoyloxy group, e.g., N,N-dimethylcarbamoyloxy, N,N-diethylcarbamoyloxy, morpholinocarbonyloxy, N,N-di-n-octylcarbamoyloxy, and N-n-octylcarbamoyloxy);

alkoxycarbonyloxy group (preferably a 2- to 30-carbon, substituted or nonsubstituted alkoxycarbonyloxy group, e.g., methoxycarbonyloxy, ethoxycarbonyloxy, t-butoxycarbonyloxy, and n-octylcarbonyloxy);

aryloxycarbonyloxy group (preferably a 7- to 30-carbon, substituted or nonsubstituted aryloxycarbonyloxy group, e.g., phenoxycarbonyloxy, p-methoxyphenoxycarbonyloxy, and p-(n-hexadecyloxy)phenoxycarbonyloxy);

amino group (preferably an amino group, 1- to 30-carbon, substituted or nonsubstituted alkylamino group, and 6- to 30-carbon, substituted or nonsubstituted anilino group, e.g., amino, methylamino, dimethylamino, anilino, N-methylanilino, and diphenylamino);

acylamino group (preferably a formylamino group, 2- to 30-carbon, substituted or nonsubstituted alkylcarbonylamino group, and 7- to 30-carbon, substituted or nonsubstituted arylcarbonylamino group, e.g., formylamino, acetylamino, pivaloylamino, lauroylamino, benzoylamino, and 3,4,5-tri-(n-octyloxy)phenylcarbonylamino);

aminocarbonylamino group (preferably 1- to 30-carbon, substituted or nonsubstituted aminocarbonylamino, e.g., carbamoylamino, N,N-dimethylaminocarbonylamino, N,N-diethylaminocarbonylamino, and morpholinocarbonylamino);

alkoxycarbonylamino group (preferably a 2- to 30-carbon, substituted or nonsubstituted alkoxycarbonylamino group, e.g., methoxycarbonylamino, ethoxycarbonylamino, t-butoxycarbonylamino, n-octadecyloxycarbonylamino, and N-methylmethoxycarbonylamino);

aryloxycarbonylamino group (preferably a 7- to 30-carbon, substituted or nonsubstituted aryloxycarbonylamino group, e.g., phenoxycarbonylamino, p-chlorophenoxycarbonylamino, and m-(n-octyloxy)phenoxycarbonylamino);

sulfamoylamino group (preferably a 0- to 30-carbon, substituted or nonsubstituted sulfamoylamino group, e.g., sulfamoylamino, N,N-dimethylsulfamoylamino, and N-n-octylsulfamoylamino);

alkylsulfonylamino and arylsulfonylamino groups (preferably 1- to 30-carbon, substituted or nonsubstituted alkylsulfonylamino and 6- to 30-carbon, substituted or nonsubstituted arylsulfonylamino, e.g., methylsulfonylamino, butylsulfonylamino, phenylsulfonylamino, 2,3,5-trichlorophenylsulfonylamino, and p-methylphenylsulfonylamino);

mercapto group;

alkylthio group (preferably a 1- to 30-carbon, substituted or nonsubstituted alkylthio group, e.g., methylthio, ethylthio, and n-hexadecylthio);

arylthio group (preferably 6- to 30-carbon, substituted or nonsubstituted arylthio, e.g., phenylthio, p-chlorophenylthio, and m-methoxyphenylthio);

heterocyclic thio group (preferably a 2- to 30-carbon, substituted or nonsubstituted heterocyclic thio group, e.g., 2-benzothiazolylthio and 1-phenyltetrazole-5-ylthio);

sulfamoyl group (preferably a 0- to 30-carbon, substituted or nonsubstituted sulfamoyl group, e.g., N-ethylsulfamoyl, N-(3-dodecyloxypropyl)sulfamoyl, N,N-dimethylsulfamoyl, N-acetylsulfamoyl, N-benzoylsulfamoyl, and N-(N'-phenylcarbamoyl)sulfamoyl);

sulfo group;

alkylsulfinyl and arylsulfinyl groups (preferably a 1- to 30-carbon, substituted or nonsubstituted alkylsulfinyl group and 6- to 30-carbon, substituted or nonsubstituted arylsulfi-nyl group, e.g., methylsulfinyl, ethylsulfinyl, phenylsulfinyl, and p-methylphenylsulfinyl);

alkylsulfonyl and arylsulfonyl groups (preferably a 1- to 30-carbon, substituted or nonsubstituted alkylsulfonyl group and 6- to 30-carbon, substituted or nonsubstituted arylsulfonyl group, e.g., methylsulfonyl, ethylsulfonyl, phenylsulfonyl, and p-methylphenylsulfonyl);

acyl group (preferably a formyl group, 2- to 30-carbon, substituted or nonsubstituted alkylcarbonyl group, 7- to 30-carbon, substituted or nonsubstituted arylcarbonyl group, and 5- to 25-carbon, substituted or nonsubstituted, 5- or 6-membered heterocyclic carbonyl group, e.g., acetyl, pivaloyl, 2-chloroacetyl, stearoyl, benzoyl, p-n-octyloxyphenylcarbonyl, and 2-pyridylcarbonyl);

aryloxycarbonyl group (preferably a 7- to 30-carbon, substituted or nonsubstituted aryloxycarbonyl group, e.g., phenoxycarbonyl, o-chlorophenoxycarbonyl, m-nitrophenoxycarbonyl, and p-t-butylphenoxycarbonyl);

alkoxycarbonyl group (preferably a 2- to 30-carbon, substituted or nonsubstituted alkoxycarbonyl group, e.g., methoxycarbonyl, ethoxycarbonyl, t-butoxycarbonyl, and n-octadecyloxycarbonyl);

carbamoyl group (preferably 1- to 30-carbon, substituted or nonsubstituted carbamoyl, e.g., carbamoyl, N-methylcarbamoyl, N,N-dimethylcarbamoyl, N,N-di-n-octylcarbamoyl, N-(methylsulfonyl)carbamoyl, and a group in which R and R' of —CON(R)R' bond to form a ring (e.g., a morpholinocarbonyl group));

arylazo and heterocyclic azo groups (preferably a 6- to 30-carbon, substituted or nonsubstituted arylazo group, and 3- to 30-carbon, substituted or nonsubstituted heterocyclic azo group, e.g., phenylazo, p-chlorophenylazo, and 5-ethylthio-1,3,4-thiadiazole-2-ylazo);

imide group (preferably N-succinimide and N-phthalimide);

phosphino group (preferably a 2- to 30-carbon, substituted or nonsubstituted phosphino group, e.g., dimethylphosphino, diphenylphosphino, and methylphenoxyphosphino);

phosphinyl group (preferably a 0- to 30-carbon, substituted or nonsubstituted phosphinyl group, e.g., phosphinyl, dioctyloxyphosphinyl, and diethoxyphosphinyl);

phosphinyloxy group (preferably a 2- to 30-carbon, substituted or nonsubstituted phosphinyloxy group, e.g., diphenoxyphosphinyloxy and dioctyloxyphosphinyloxy);

phosphinylamino group (preferably a 2- to 30-carbon, substituted or nonsubstituted phosphinylamino group, e.g., dimethoxyphosphinylamino and dimethylaminophosphinylamino); and silyl group (preferably a 3- to 30-carbon, substituted or nonsubstituted silyl group, e.g., trimethylsilyl, t-butyldimethylsilyl, and phenyldimethylsilyl).

Of the above functional groups, those having a hydrogen atom can be further substituted by the above groups by removing the hydrogen atom. Examples of such functional groups are an alkylcarbonylaminosulfonyl group, arylcarbonylaminosulfonyl group, alkylsulfonylaminocarbonyl group, and arylsulfonylaminocarbonyl group. More specific examples are methylsulfonylaminocarbonyl, p-methylphenylsulfonylaminocarbonyl, acetylaminosulfonyl, and benzoylaminosulfonyl groups.

When $L^1$ is an alkylene group, this alkylene group is preferably a 1- to 30-carbon, substituted or nonsubstituted alkylene group which can be straight-chain, branched, or cyclic. This alkylene group is more preferably a 1- to 10-carbon, nonsubstituted alkylene group, and most preferably a 1- to 6-carbon, nonsubstituted alkylene group. Examples are methylene, 1,2-ethylene, 1,3-propylene, 1-methylmethylene, 1,1-dimethylmethylene, 1,1,2,2-tetramethyl-1,2-ethylene, 1,4-butylene, 1,4-cyclohexylene, and 1-phenylmethylene.

When $L^1$ is an arylene group, this arylene group is preferably a 6- to 35-carbon, substituted or nonsubstituted arylene group, and more preferably a 6- to 12-carbon, substituted or nonsubstituted arylene group. Examples are 1,2-phenylene, 1,3-phenylene, 1,4-phenylene, and 2,4,6-trimethyl-1,3-phenylene. $L^1$ is preferably an alkylene group, rather than an arylene group.

Practical examples of $L^1$ are presented below, but the present invention is not limited to these examples. In these formulas, a symbol * indicates the position where $L^1$ bonds to a pyrazoloazole ring.

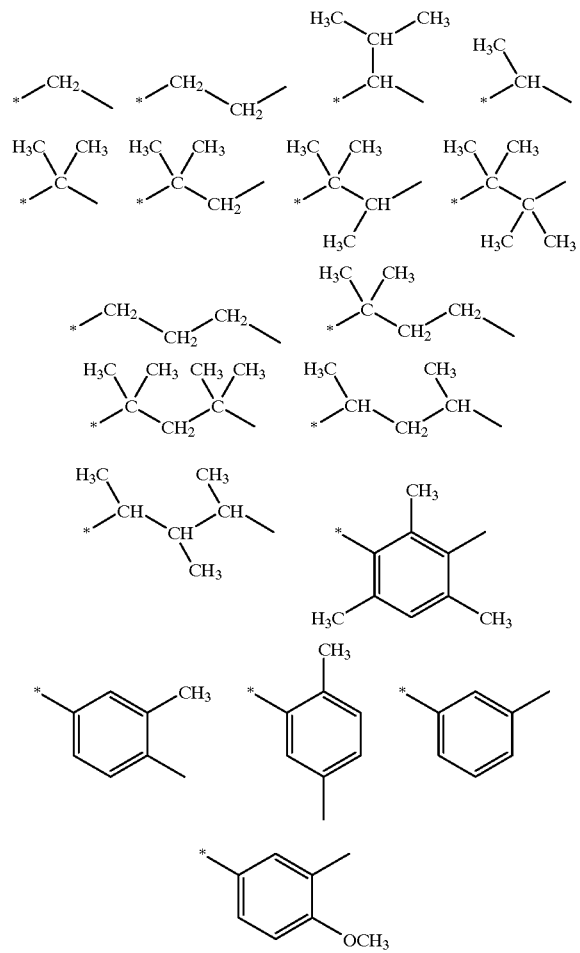

In formula (M-1), $L^2$ represents a substituted or nonsubstituted alkylene group or substituted or nonsubstituted arylene group. Examples of a substituent when this alkylene group or arylene group is substituted are those enumerated above as substituents for substituting $L^1$.

When $L^2$ is an alkylene group, this alkylene group is preferably a 1- to 30-carbon, substituted or nonsubstituted alkylene group which can be straight-chain, branched, or cyclic. This alkylene group represented by $L^2$ is more preferably a 1- to 25-carbon, substituted or nonsubstituted alkylene group, and the number of carbon atoms is more preferably 1 to 20. A 1- to 6-carbon, nonsubstituted alkylene group is particularly preferred. Examples are 1,2-ethylene, 1,4-butylene, 1,14-tetradecylene, 1,4-cyclohexylene, 1-phenylmethylene, and 2-ethyl-1,6-cyclohexylene.

When $L^2$ is an arylene group, this arylene group is preferably a 6- to 40-carbon, substituted or nonsubstituted arylene group, and more preferably a 6- to 30-carbon, substituted or nonsubstituted arylene group, and the number of carbon atoms is more preferably 6 to 25. Examples are 1,2-phenylene, 1,3-phenylene, 1,4-phenylene, 2-butoxy-1,5-phenylene, 2-octyloxy-1,5-phenylene, 2-hexadecyloxy-1,5-phenylene, 4-methoxyphenoxy-1,5-phenylene, 4-chloro-1,5-phenylene, 2-methoxyethoxy-1,5-phenylene, 2-hexadecyl-1,5-phenylene, 4-hexadecyl-1,5-phenylene, 4-hexadecyloxy-1,5-phenylene, 2-hexadecyloxy-1,4-phenylene, 2-methylcyclohexyloxy-1,5-phenylene, 2-benzyloxy-1,5-phenylene, and 2-octadecyloxy-1,5-phenylene. The 1-position of any of these arylene groups bonds to the right side of an —$L^1$—NH—CO— group of formula (M-1).

Practical examples of $L^2$ are presented below, but the present invention it not limited to these examples. In these formulas, a symbol * indicates the position where $L^2$ bonds to the right side of an —$L^1$—NH—CO— group of formula (M-1).

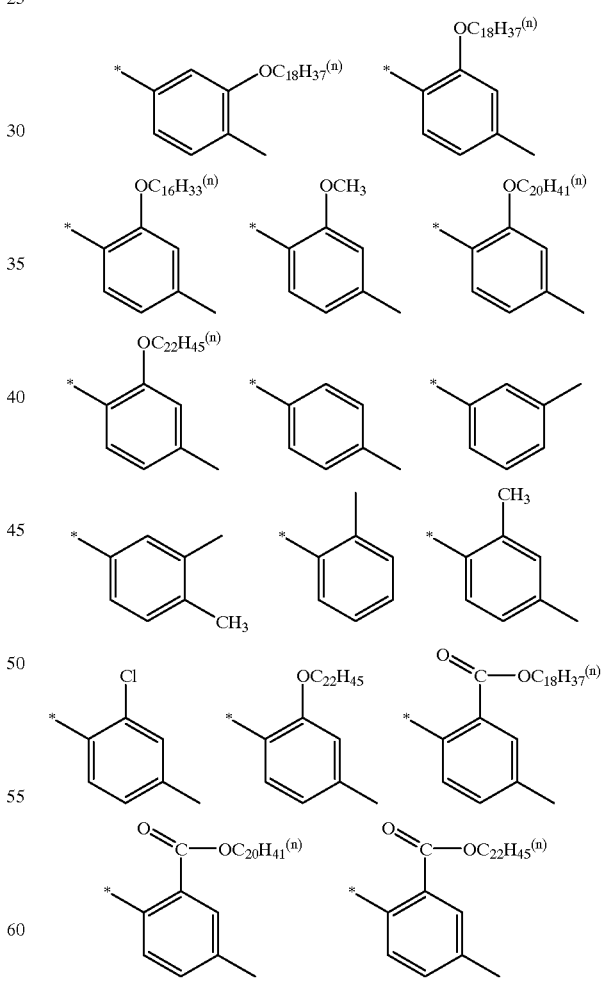

$L^2$ is preferably an arylene group, rather than an alkylene group. Also, $L^2$ is preferably substituted. This substituent is preferably an alkoxy group, aminocarbonyl group, halogen atom, or alkyl group.

$L^3$ represents —NH—SO$_2$— or —CO—NH—SO$_2$— (In these representations, bonding direction is not defined. More specifically, either the left side or the right side of —NH—SO$_2$— can bond to $L^2$, or either the left side or the right side of —CO—NH—SO$_2$— can bond to $L^2$). Alternatively, $L^3$—G represents —COOH or —OH.

$L^3$ is preferably —NH—SO$_2$—. The left side of —NH—SO$_2$— preferably bonds to NH—CO—$L^2$, and the right side of —NH—SO$_2$— preferably bonds to G.

X represents a hydrogen atom or a group which splits off when coupling with an oxidized form of a developing agent. Practical examples are a halogen atom, alkoxy group, aryloxy group, acyloxy group, alkylsulfonyloxy or arylsulfonyloxy group, acylamino group, alkylsulfonylamino or arylsulfonylamino group, alkoxycarbonyloxy group, alkylthio, arylthio, or heterocyclic thio group, carbamoyl group, carbamoyloxy group, heterocyclic carbonyloxy group, 5- or 6-membered, nitrogen-containing heterocyclic group, imide group, arylazo group, and alkyl group {e.g., a group represented by formula —CR$^{21}$(R$^{22}$)—NH—SO$_2$—R$^{23}$ (each of R$^{21}$ and R$^{22}$ independently represents a hydrogen atom, substituted or nonsubstituted alkyl group, or substituted or nonsubstituted aryl group, and R$^{23}$ represents a substituted or nonsubstituted alkyl group or substituted or nonsubstituted aryl group)}.

X is preferably a hydrogen atom, halogen atom, alkoxy group, aryloxy group, alkylthio or arylthio group, alkyloxycarbonyloxy group, aryloxycarbonyloxy group, or carbamoyloxy group, more preferably a hydrogen atom, halogen atom, 6- to 30-carbon arylthio group, or 6- to 30-carbon aryloxy group, and most preferably a hydrogen atom.

G represents a substituted or nonsubstituted alkyl group or substituted or nonsubstituted aryl group. Examples of a substituent for substituting these alkyl and aryl groups are those enumerated above as substituents for substituting $L^1$ and $L^2$. G is preferably a 1- to 30-carbon, substituted or nonsubstituted alkyl group or 6- to 30-carbon, substituted or nonsubstituted aryl group, and more preferably a 6- to 30-carbon, substituted or nonsubstituted aryl group. This aryl group is preferably substituted. This substituent is preferably a 2- to 10-carbon alkoxycarbonyl group (including a cycloalkoxycarbonyl group), an aminocarbonyl group substituted by 1- to 10-carbon alkyl, a halogen atom, or a 1- to 20-carbon alkyl group.

In formula (M-1), n represents 1 or 2 when $L^2$ is an alkylene group, and represents an integer from 1 to 5 when $L^2$ is an arylene group. When n is 2 or more, a plurality of —$L^3$—G's can be the same or different. n is preferably 1 or 2.

In a preferred structure of formula (M-1), $R^1$ is a 1- to 10-carbon, straight-chain, branched, or cyclic, nonsubstituted alkyl group, $L^1$ is a 1- to 10-carbon, nonsubstituted alkylene group, $L^2$ is a 6- to 30-carbon, substituted or nonsubstituted arylene group, $L^3$ is —NH—SO$_2$— (the left side bonds to NH—CO—$L^2$ and the right side bonds to G), n is 1 or 2, X is a hydrogen atom, halogen atom, 6- to 30-carbon arylthio group, or 6- to 30-carbon aryloxy group, and G is a 6- to 30-carbon, substituted or nonsubstituted aryl group.

A coupler represented by formula (M-1) preferably has a structure represented by formula (M-2) below.

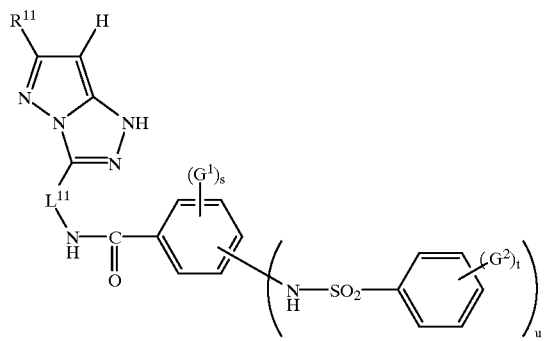

(M-2)

In formula (M-2), $R^{11}$ is a 1- to 6-carbon, nonsubstituted alkyl group. Practical examples of $R^{11}$ are methyl, ethyl, n-propyl, isopropyl, t-butyl, and t-octyl. $R^{11}$ is preferably isopropyl or t-butyl and most preferably t-butyl.

$L^{11}$ is a 1- to 6-carbon, nonsubstituted alkylene group. Practical examples are methylene, 1,2-ethylene, 1,3-propylene, 1-methylmethylene, 1-isopropylmethylene, 1,1-dimethylmethylene, 1,1,2,2-tetramethyl-1,2-ethylene, 1,4-butylene, and 1,4-cyclohexylene. $L^{11}$ is most preferably 1-methylmethylene.

Each of $G^1$ and $G^2$ independently represents a substituted or nonsubstituted alkyl group, substituted or nonsubstituted alkoxy group, substituted or nonsubstituted aryloxy group, halogen atom, substituted or nonsubstituted acylamino group, substituted or nonsubstituted alkoxycarbonyl group (including a cycloalkyloxycarbonyl group), or substituted or nonsubstituted aminocarbonyl group.

$G^1$ is preferably a 1- to 30-carbon, nonsubstituted alkyl group (e.g., methyl or t-octyl), 1- to 30-carbon, nonsubstituted alkoxy group (e.g., methoxy, n-octyloxy, or n-octadecyloxy), 6- to 30-carbon, nonsubstituted aryloxy group (e.g., phenoxy or p-methoxyphenoxy), or 2- to 31-carbon alkoxycarbonyl group (e.g., methoxycarbonyl, n-octyloxycarbonyl, or n-octadecyloxycarbonyl). $G^1$ is most preferably a 1- to 22-carbon, nonsubstituted alkoxy group.

It is preferable that $G^1$ bond to the phenylene group in an ortho-position to —$L^{11}$—NH—CO— in formula (M-2).

$G^2$ is preferably a halogen atom (e.g., chlorine, bromine, or iodine), 1- to 30-carbon, nonsubstituted acylamino group (e.g., formylamino, acetylamino, or pivaloylamino), 2- to 30-carbon, nonsubstituted alkoxycarbonyl group (e.g., methoxycarbonyl, ethoxycarbonyl, n-octyloxycarbonyl, or cyclohexyloxycarbonyl), or 1- to 30-carbon aminocarbonyl group which is nonsubstituted or substituted by an alkyl group (e.g., carbamoyl, dimethylcarbamoyl, n-octylcarbamoyl, or piperidinocarbonyl). $G^2$ is most preferably a 2- to 10-carbon, nonsubstituted alkoxycarbonyl group or 2- to 10-carbon aminocarbonyl group substituted by an alkyl group.

When t is 1, it is preferable that $G^2$ bond to the phenyl group in a meta-position to —NH—SO$_2$— in formula (M-2). When t is 2, it is preferable that two $G^2$'s bond to the phenyl group in two meta-positions to —NH—SO$_2$— in formula (M-2).

s represents an integer from 0 to 4, t represents an integer from 0 to 5, and u represents 1 or 2. The sum of s and u does not exceed 5. s is preferably 0 or 1, t is preferably 1 or 2, and u is preferably 1.

In a magenta coupler represented by formula (M-2), the value of pKa of —NHSO$_2$— between the two phenyl groups at 25° C. in a solution of THF/H$_2$O=6/4 is 12 or less, preferably 11 or less. This pKa is preferably 5 or more, more preferably 7 or more, and most preferably 9 or more.

The pKa is preferably 5 to 12, more preferably 7 to 11, and most preferably 9 to 10.5.

In a magenta coupler represented by formula (M-2), when both substituents G$^1$ and G$^2$ of the phenyl groups are alkyl groups or alkoxy groups, the value of pKa exceeds 12.

A coupler having a pKa value of 12 or less has high color forming efficiency even when used without any oil, and has a small effect on the color forming efficiency caused by variations in the pH of a processing solution.

In practical examples CP-2 and CP-5 to be presented later of a magenta coupler, pKa values are 10.4 and 10.9, respectively.

In formula (M-2), the left side of —NH—SO$_2$— bonds to the phenyl group in arbitrary position to form the phenylene group. Preferably, the left side of —NH—SO$_2$— bonds to the phenyl group in a meta-position to —L$^{11}$—NH—CO— in formula (M-2).

A coupler having a structure represented by formula (M-1) of the present invention more preferably has a structure represented by formula (M-3) below. A coupler having this structure is a novel compound.

(M-3)

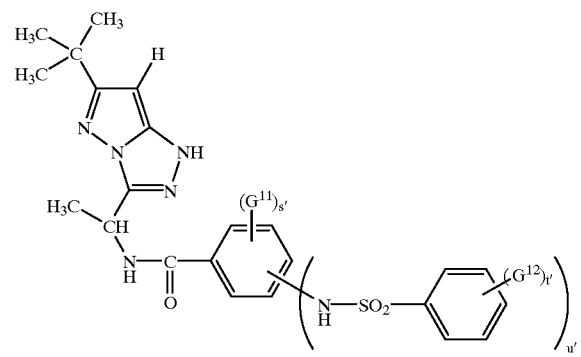

In formula (M-3), each of G$^{11}$ and G$^{12}$ independently represents a 1- to 30-carbon, substituted or nonsubstituted alkyl group, 1- to 30-carbon, substituted or nonsubstituted alkoxy group, 6- to 30-carbon, substituted or nonsubstituted aryloxy group, halogen atom, 1- to 30-carbon, substituted or nonsubstituted acylamino group, 2- to 30-carbon, substituted or nonsubstituted alkoxycarbonyl group, or 1- to 30-carbon, substituted or nonsubstituted aminocarbonyl group. Practical examples of substituents G$^{11}$ and G$^{12}$ are those enumerated above for G$^1$ and G$^2$ in formula (M-2).

G$^{11}$ is preferably a 1- to 30-carbon, substituted or nonsubstituted alkyl group, 1- to 30-carbon, substituted or nonsubstituted alkoxy group, or 6- to 30-carbon, substituted or nonsubstituted aryloxy group. G$^{11}$ is more preferably a 1- to 22-carbon, nonsubstituted alkoxy group, and most preferably n-hexadecyloxy, n-octadecyloxy, n-eicosyloxy, or n-dieicosyloxy.

It is preferable that G$^{11}$ bond to the phenylene group in an ortho-position to —CH(CH$_3$)—NH—CO— in formula (M-3).

G$^{12}$ is preferably a halogen atom, 1- to 30-carbon, substituted or nonsubstituted acylamino group, 2- to 30-carbon, substituted or nonsubstituted alkoxycarbonyl group, or 1- to 30-carbon, substituted or nonsubstituted aminocarbonyl group. G$^{12}$ is more preferably a 2- to 10-carbon, nonsubstituted alkoxycarbonyl group or 2- to 10-carbon, nonsubstituted alkylaminocarbonyl group.

When t' is 1, it is preferable that G$^{12}$ bond to the phenyl group in a meta-position to —NH—SO$_2$— in formula (M-3). When t' is 2, it is preferable that two G$^{12}$'s bond to the phenyl group in two meta-positions to —NH—SO$_2$— in formula (M-3).

s' represents an integer from 0 to 4, t' represents an integer from 0 to 5, and u' represents 1 or 2. The sum of s' and u' does not exceed 5. s' is preferably 0 or 1, t' is preferably 1 or 2, and u' is preferably 1.

In formula (M-3), the left side of —NH—SO$_2$— bonds to the phenyl group in arbitrary position to form the phenylene group. Preferably, the left side of —NH—SO$_2$— bonds to the phenyl group in a meta-position to —CH(CH$_3$)—NH—CO— in formula (M-3).

The measurement of the pKa value in the present invention will be described below. The pKa value was measured under the following conditions by using the AT-210 measurement device (Kyoto Denshi Kogyo K.K.) That is, 1×10$^{-5}$ mL of a magenta coupler of the present invention was accurately weighed at room temperature (25° C.) and dissolved in 30 mL of THF. 20 mL of H$_2$O were then added to completely dissolve the material. Subsequently, 0.25 mL of an aqueous 0.2 N hydrochloric acid solution was added, and the resultant solution was stirred. This solution was titrated with an aqueous 0.2 N NaOH solution, and the pKa value was obtained from the middle point of neutralization. All pKa values in the present invention were obtained under the above measurement conditions.

Compound examples of the present invention are presented below, but the present invention is not restricted to these examples.

Exemplified Compounds (CP-1–CP-3)

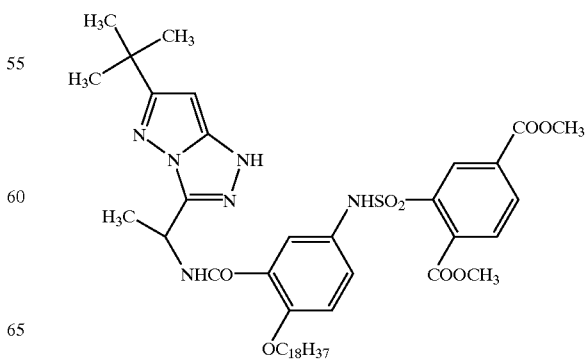

CP-1

CP-2
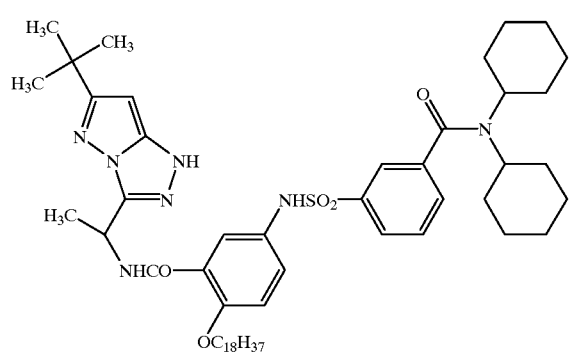
CP-5
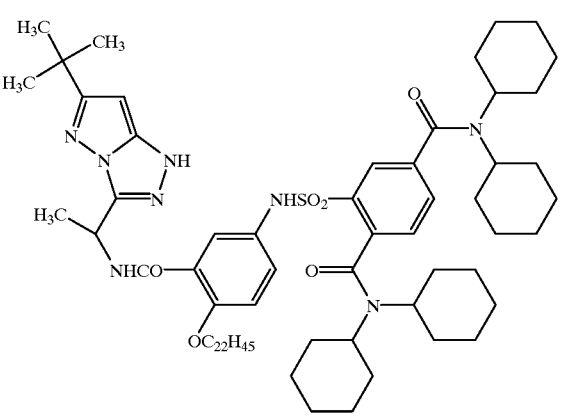
CP-3
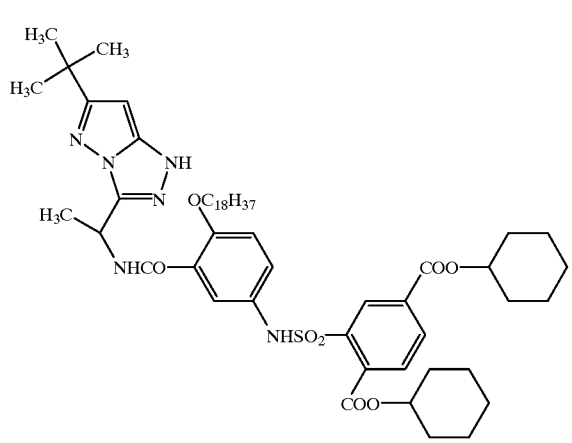
CP-6
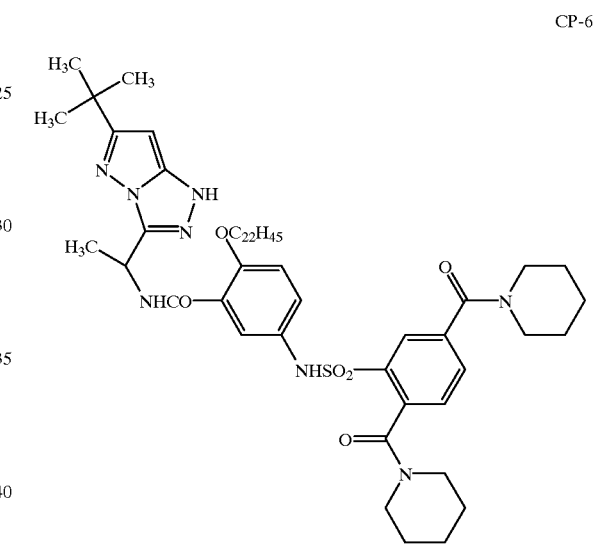
Exemplified Compounds (CP-4–CP-6)
Exemplified Compounds (CP-7–CP-9)
CP-4
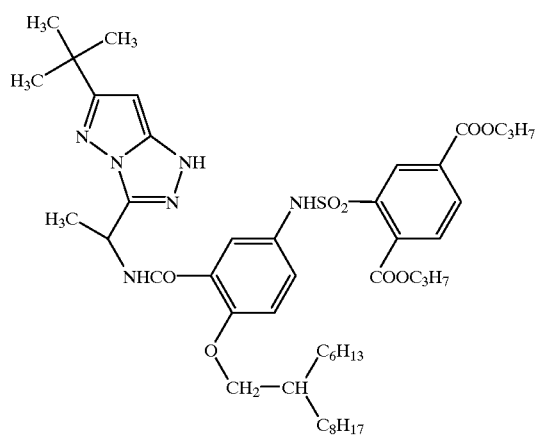
CP-7
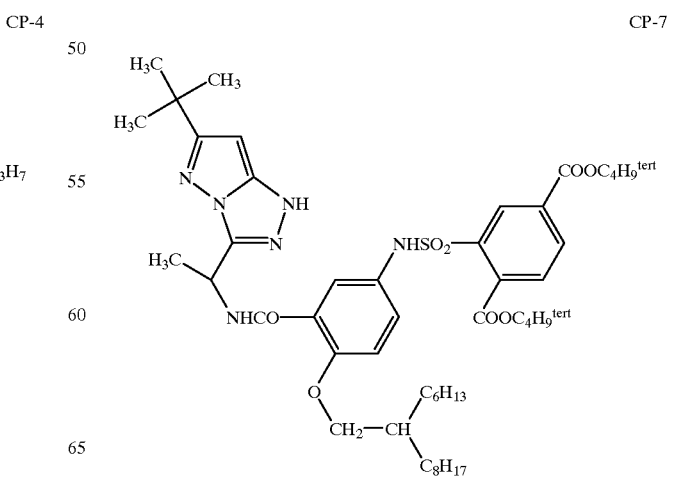

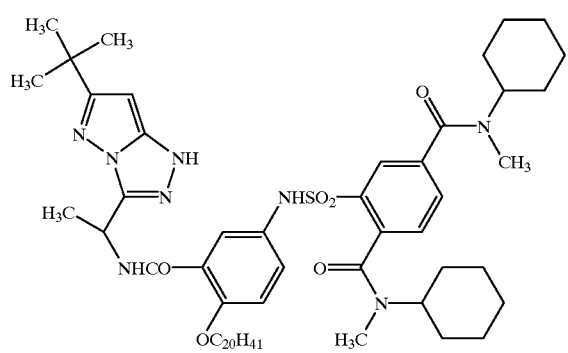
CP-8
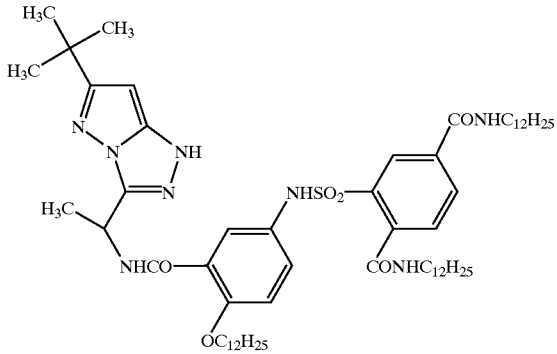
CP-11
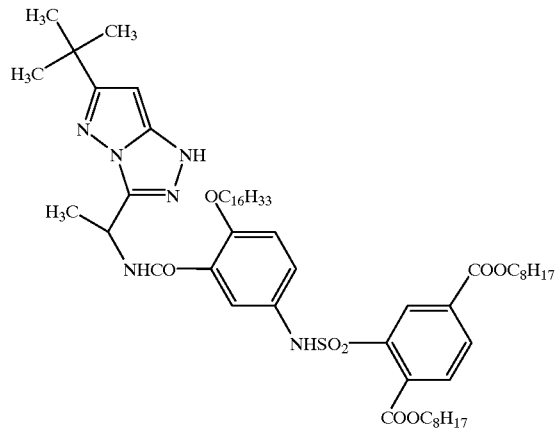
CP-9
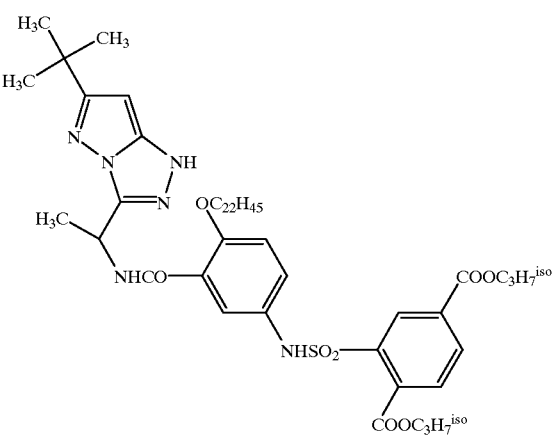
CP-12
Exemplified Compounds (CP-10–CP-12)
Exemplified Compounds (CP-13–CP-15)
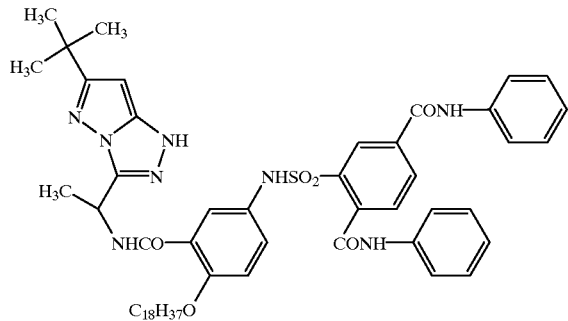
CP-10
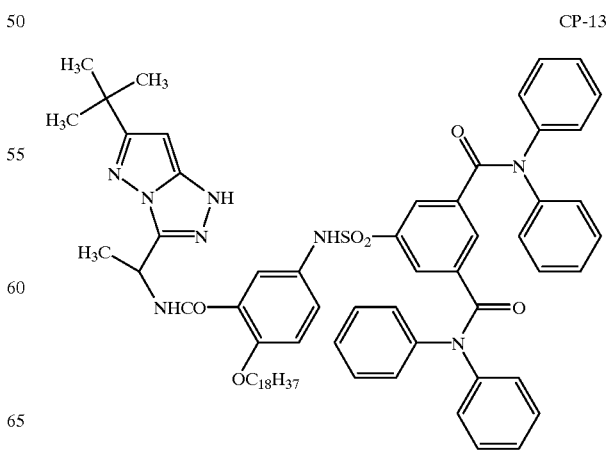
CP-13

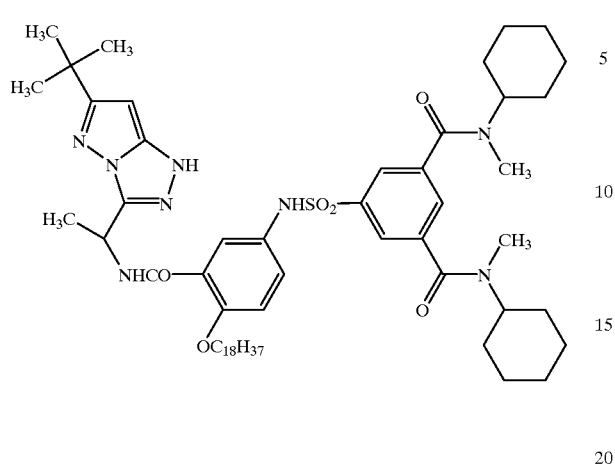
CP-14
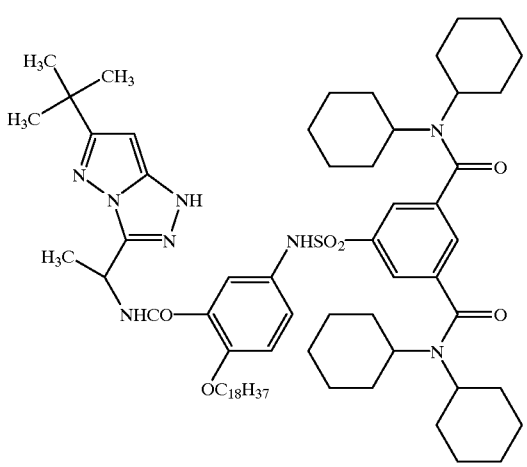
CP-17
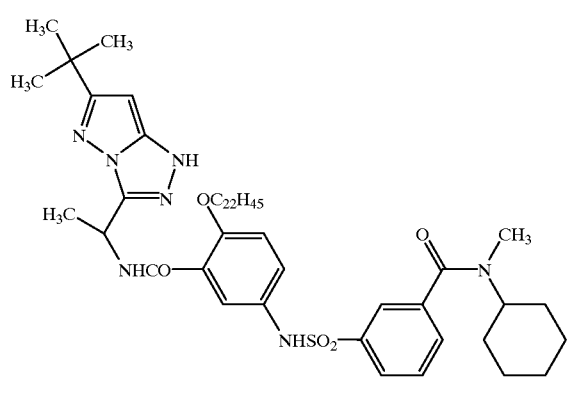
CP-15
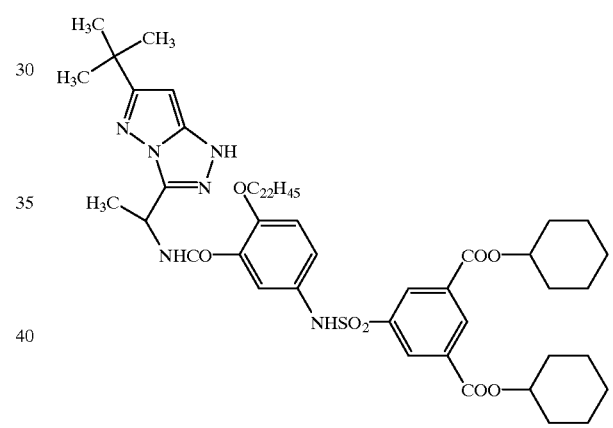
CP-18
Exemplified Compounds (CP-16–CP-18)
Exemplified Compounds (CP-19–CP-21)
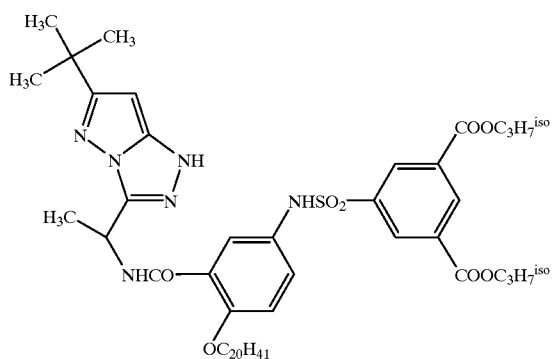
CP-16
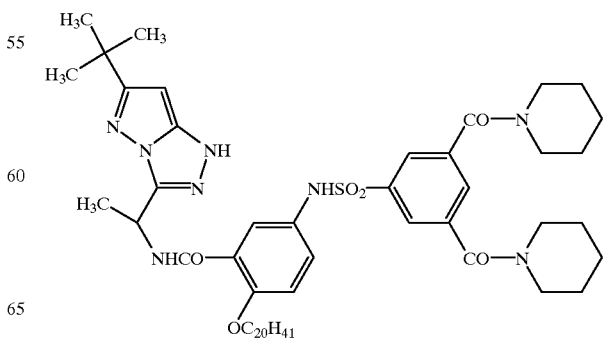
CP-19

Exemplified Compounds (CP-22–CP-24)

Exemplified Compounds (CP-25–CP-27)

-continued
CP-26
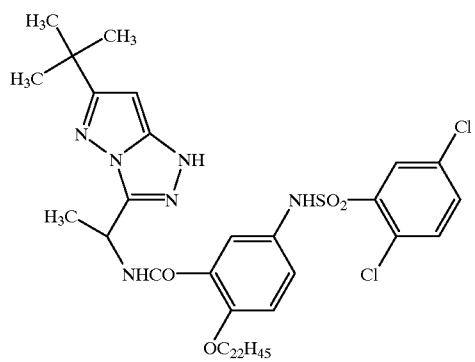
CP-29
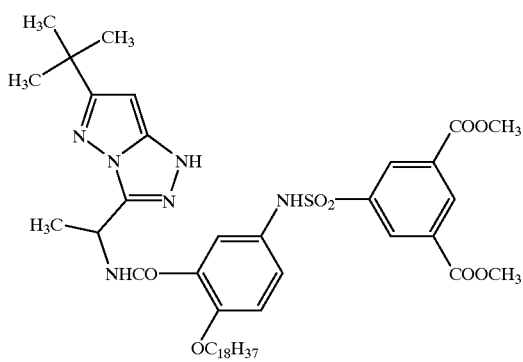
CP-27
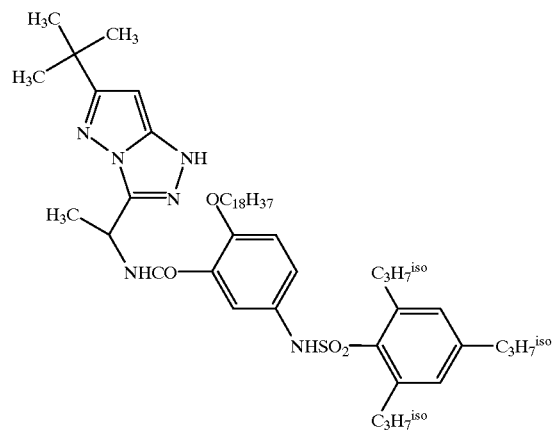
CP-30
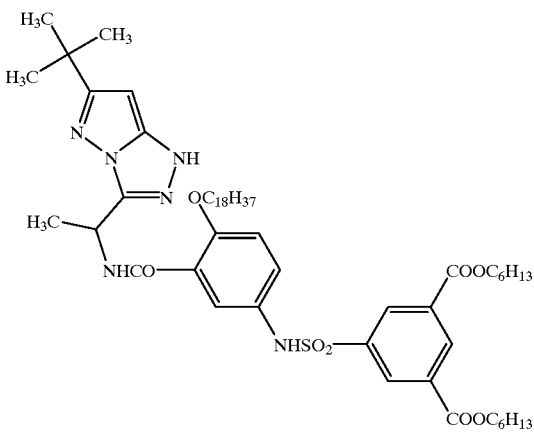
Exemplified Compounds (CP-31–CP-33)
Exemplified Compounds (CP-28–CP-30)
CP-28
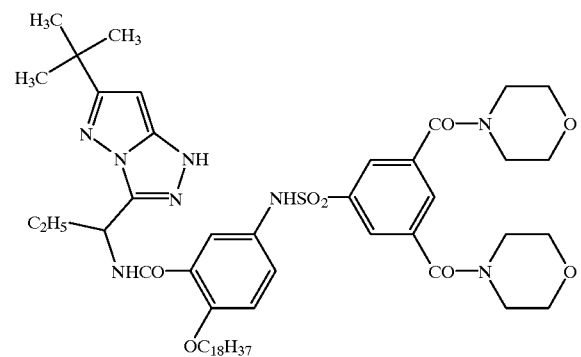
CP-31
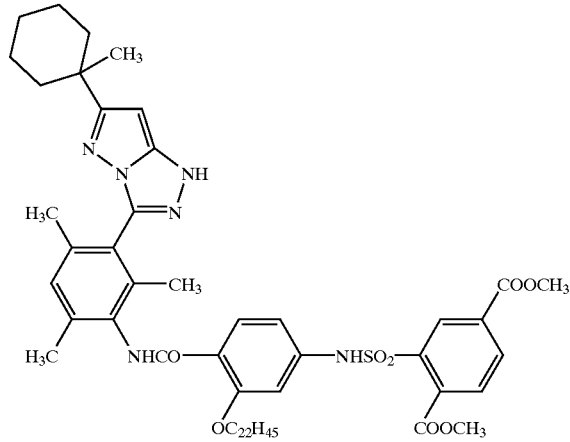

-continued
CP-32
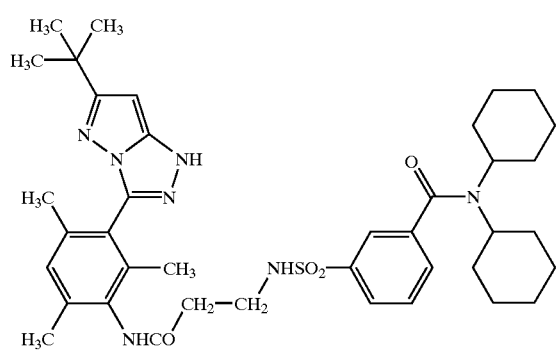
CP-35
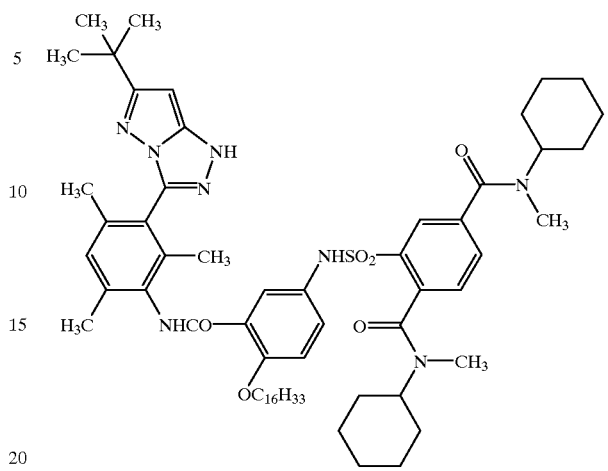
CP-33
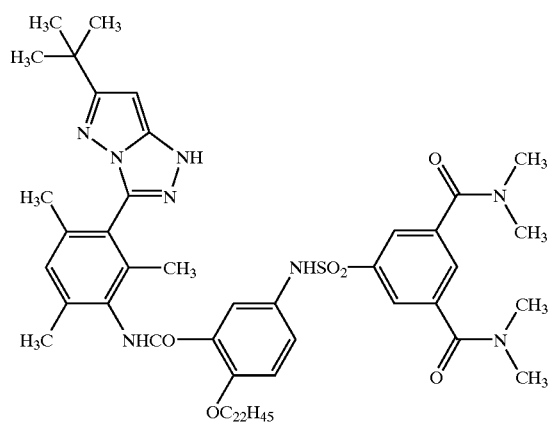
CP-36
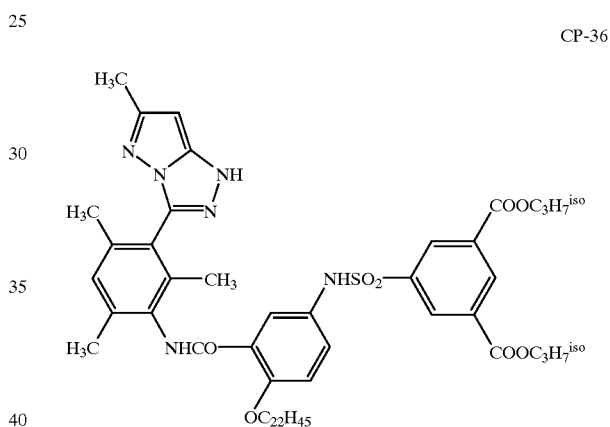
Exemplified Compounds (CP-34–CP-36)
Exemplified Compounds (CP-37–CP-39)
CP-34
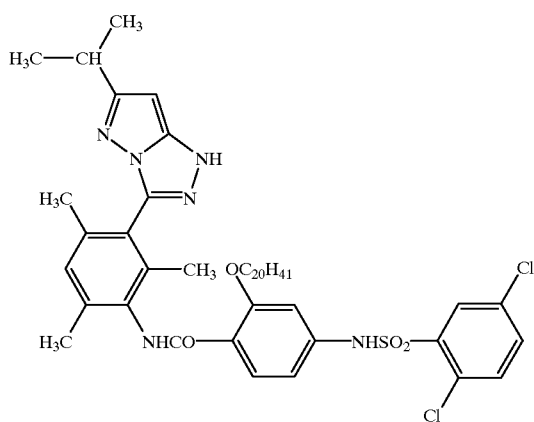
CP-37
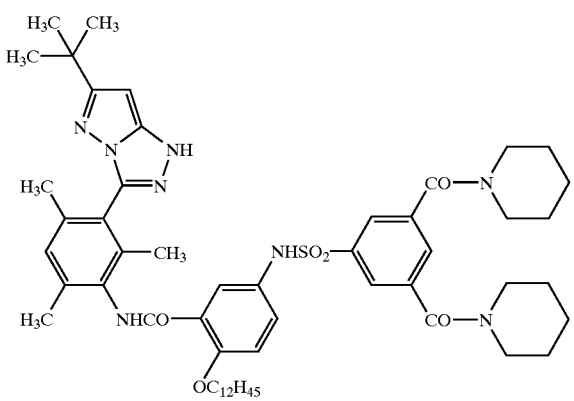

CP-38
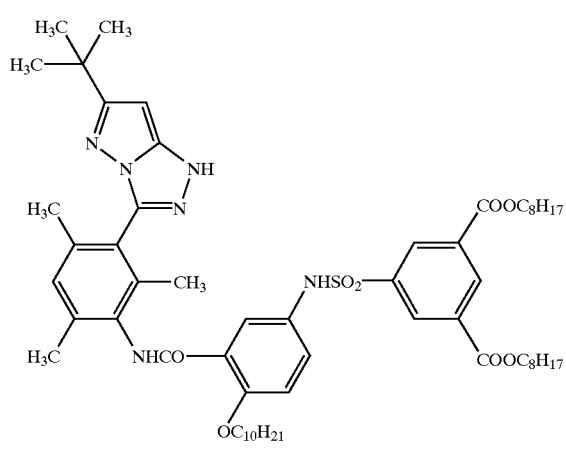
CP-41
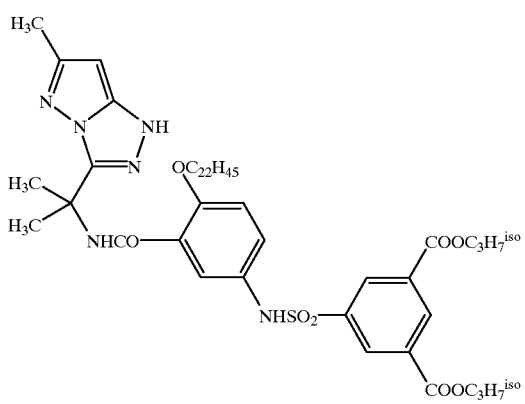
CP-39
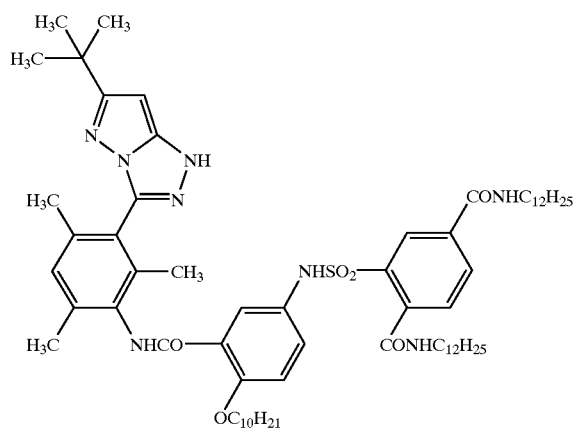
CP-42
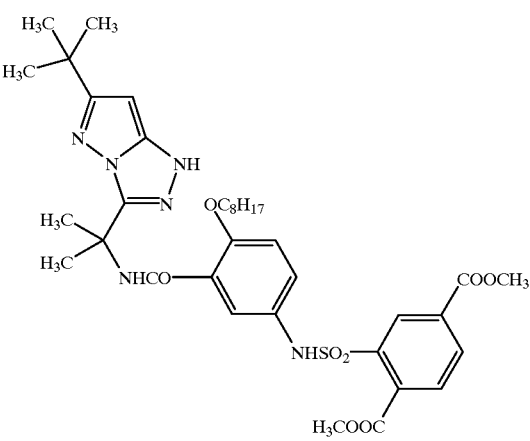
Exemplified Compounds (CP-40–CP-42)
CP-40
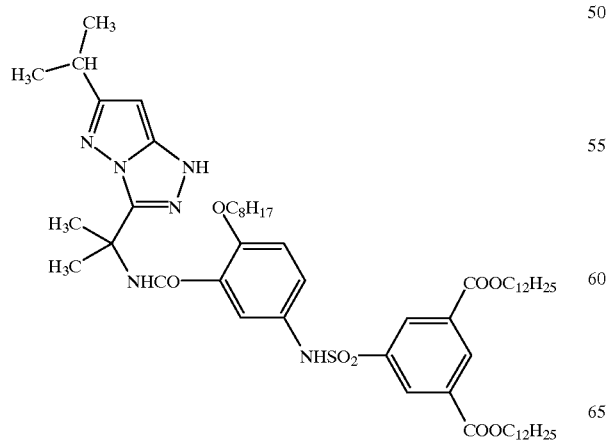
Exemplified Compounds (CP-43–CP-45)
CP-43
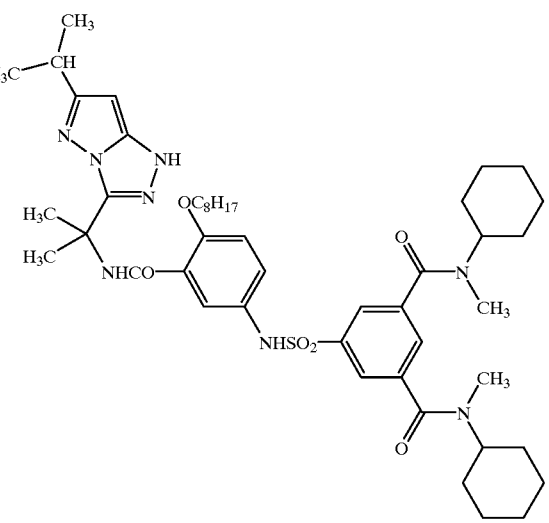

CP-44
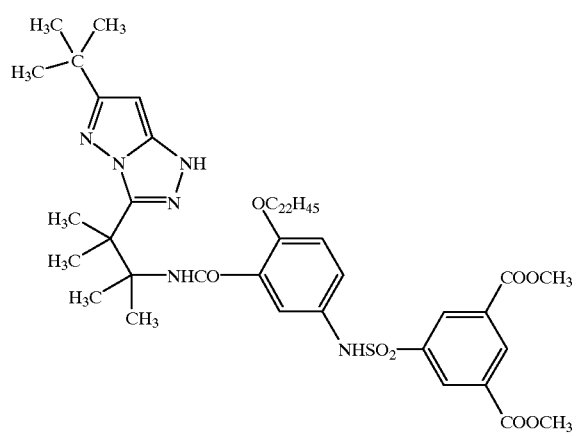
CP-45
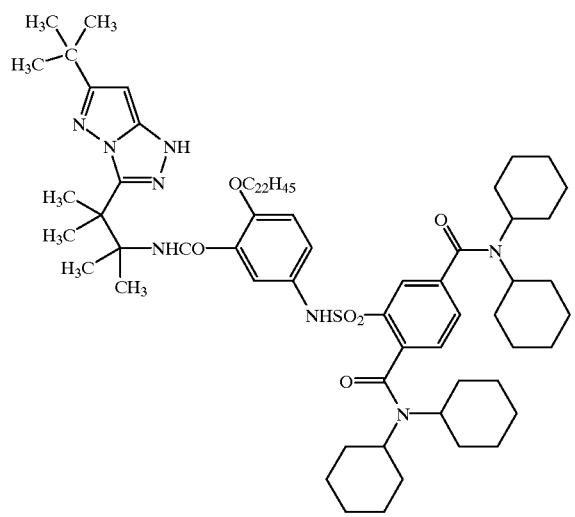
Exemplified Compounds (CP-46–CP-48)
CP-46
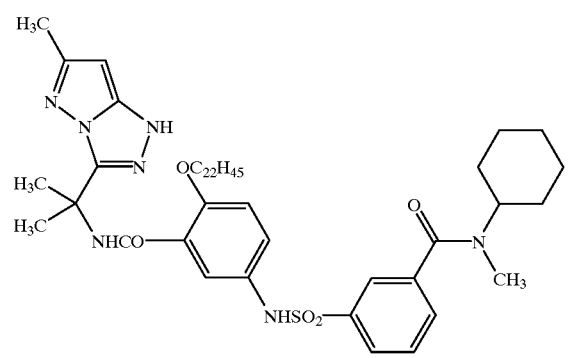
CP-47
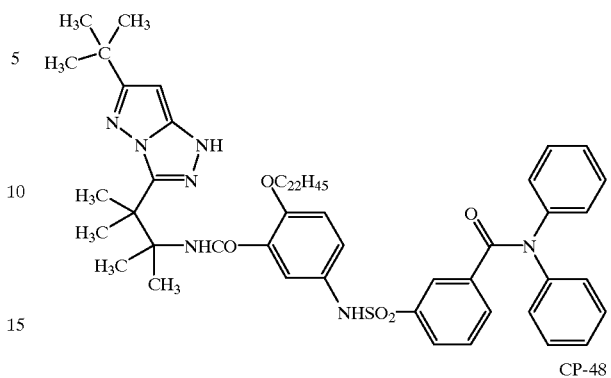
CP-48
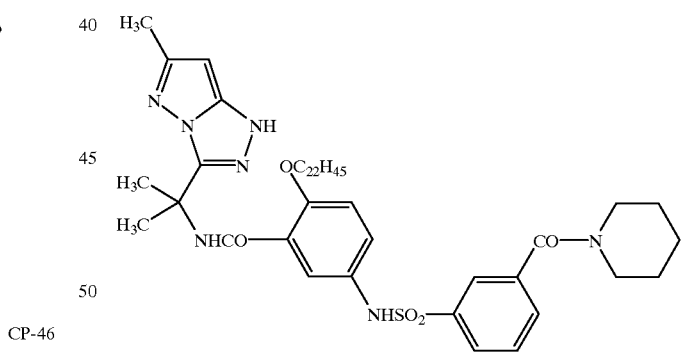
Exemplified Compounds (CP-49–CP-51)
CP-49
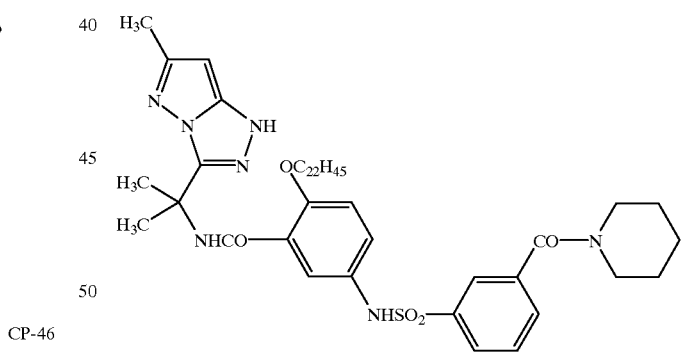
CP-50
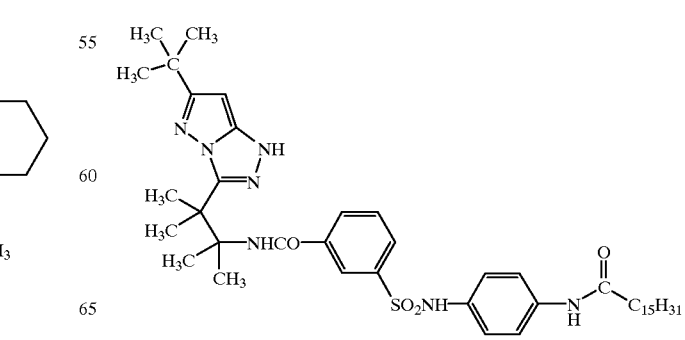

CP-51
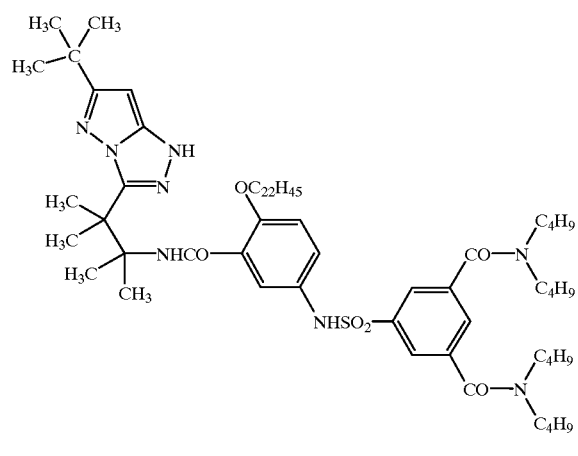
CP-54
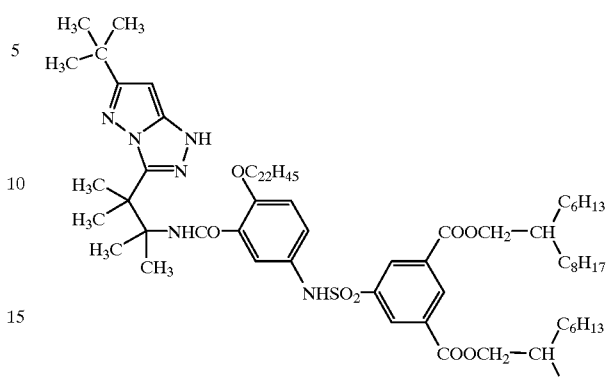
Exemplified Compounds (CP-52–CP-54)
CP-52
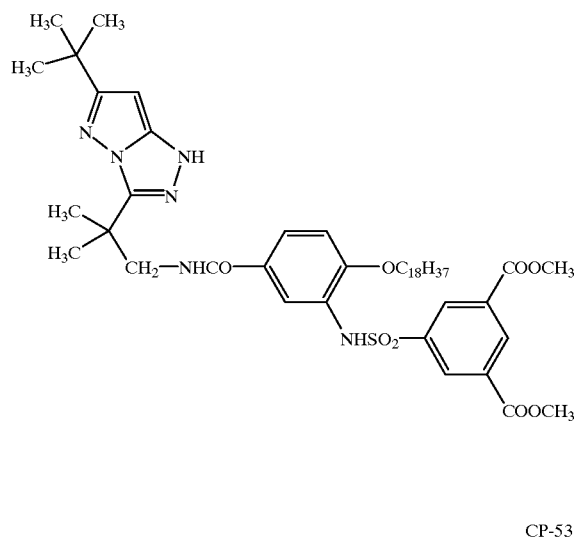
Exemplified Compounds (CP-55–CP-57)
CP-55
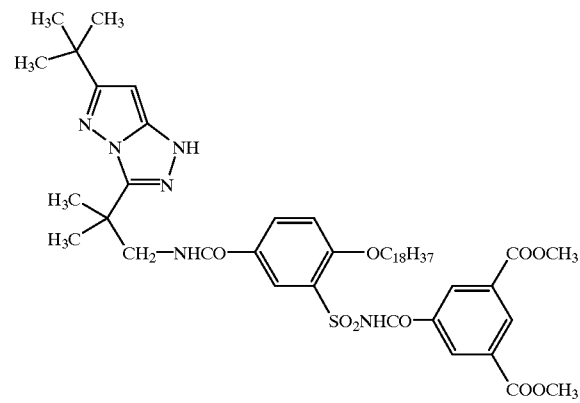
CP-53
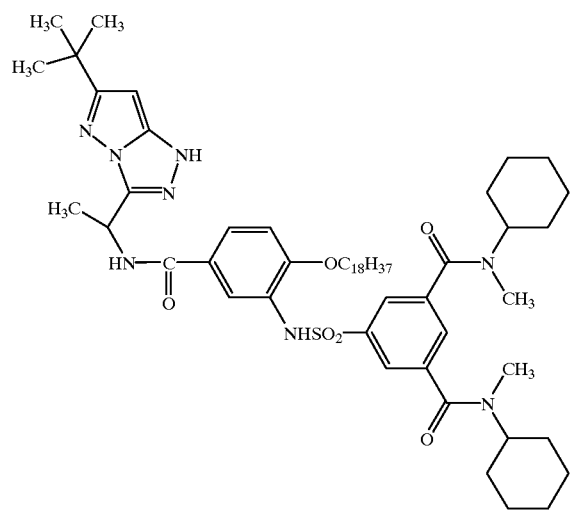
CP-56

-continued
CP-57
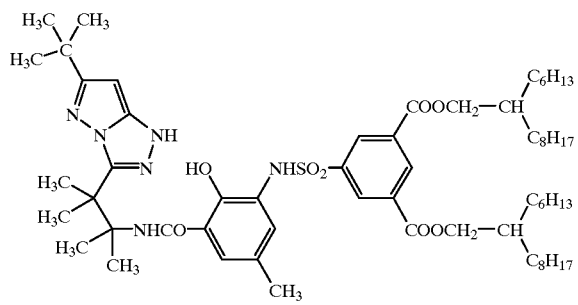
Exemplified Compounds (CP-58–CP-60)
CP-58
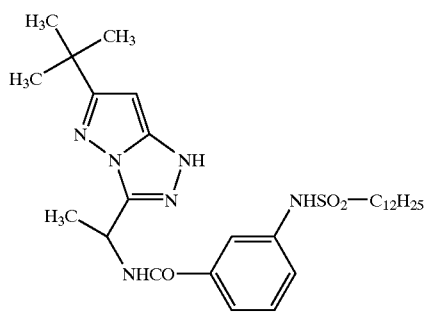
CP-59
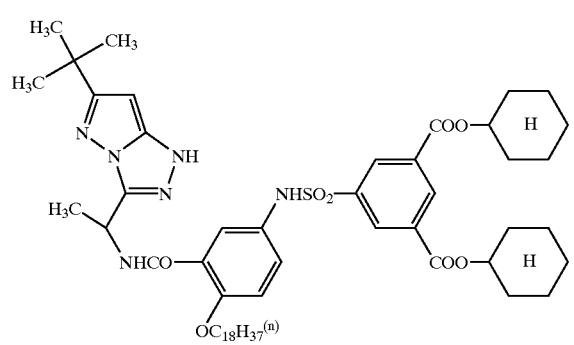
CP-60
Exemplified Compounds (CP-61–CP-63)
CP-61
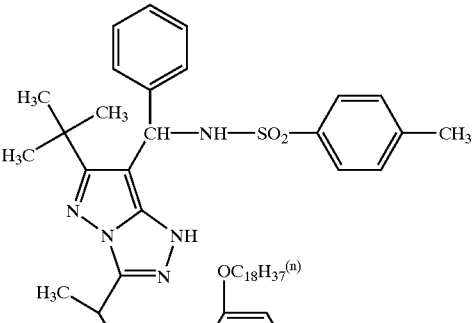
CP-62
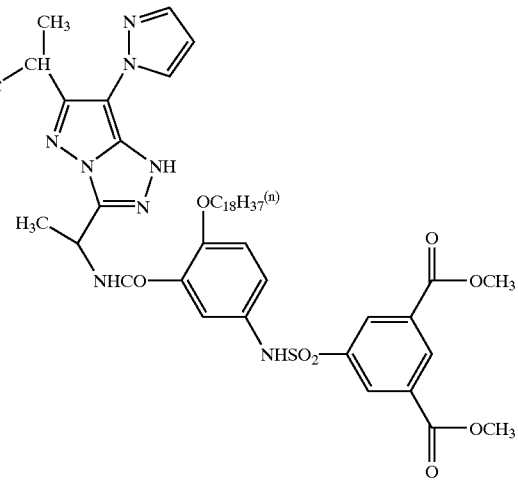
CP-63
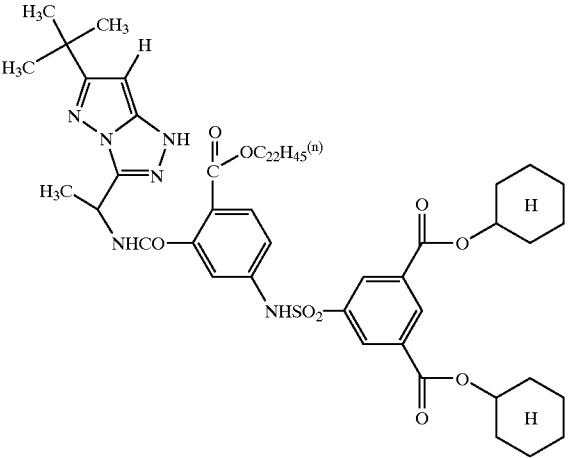

Exemplified Compounds (CP-64–CP-65)

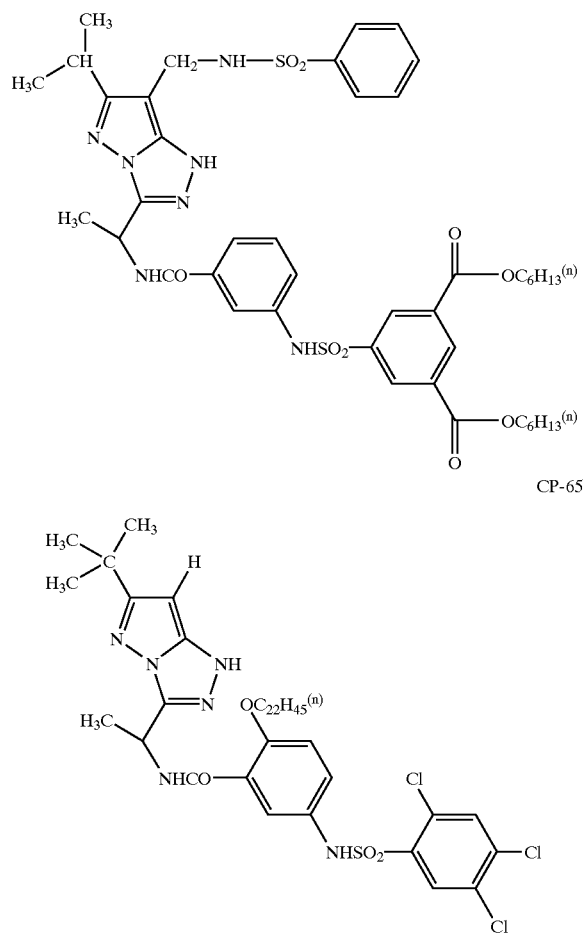

All coupler compounds CP-1 to CP-65 described above come within the category of formula (M-1). Compounds falling under the category of formula (M-2) are CP-1 to CP-30, CP-40 to CP-49, CP-51 to CP-54, CP-60, CP-63, and CP-65. Compounds falling under the category of formula (M-3) are CP-1 to CP-27, CP-29, CP-30, CP-53, CP-60, CP-63, and CP-65.

Methods of synthesizing compounds of the present invention will be described below, and the present invention will be explained in more detail below. Although synthesis examples 1 to 6 of compounds of the present invention will be described, other compounds can also be synthesized by similar methods.

The present invention will be described in more detail below by way of synthesis examples.
{General Synthesis Method}

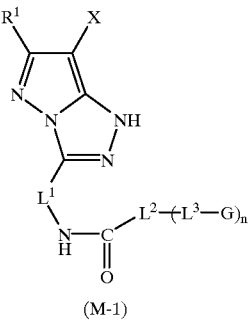

The coupler represented by formula (M-1) is synthesized by condensing an intermediate α (coupler nucleus amino body) and an intermediate β (ballast group intermediate). Staged synthesis can also be performed depending on the structure of the coupler. These couplers can be easily synthesized by applying known methods of coupler synthesis.

{In the formula, $R^1$, X, $L^1$, $L^2$, $L^3$, G, and n have the same meanings as $R^1$, X, $L^1$, $L^2$, $L^3$, G, and n in formula (M-1) of claims. $x^2$ is a split-off group in the field of organic synthesis. Examples of the split-off group are a chlorine atom, a bromine atom, OH, a sulfonyloxy group, an acyloxy group, and a hydroxyl group activated by a condensing agent.}

When $X^2$ is a chlorine atom, a 1-equivalent base is preferably used for condensing the intermediates α and β.

Practical synthesis examples will be explained below.

Synthesis Example 1
(Synthesis of Exemplified Compound CP-1)

Synthesis of intermediate A

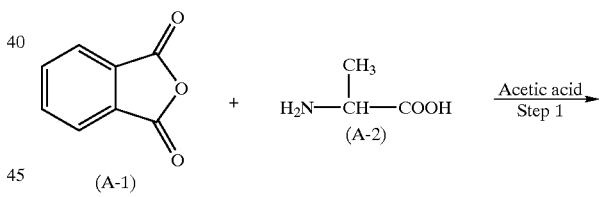

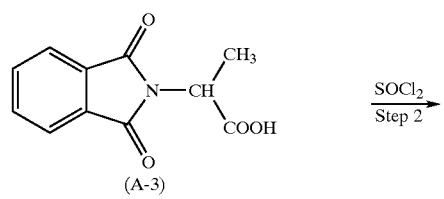

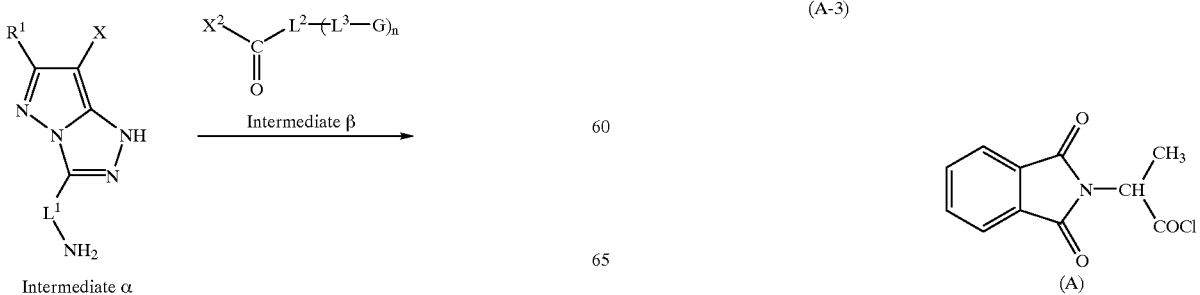

Synthesis of intermediate B
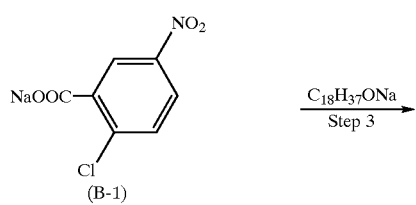
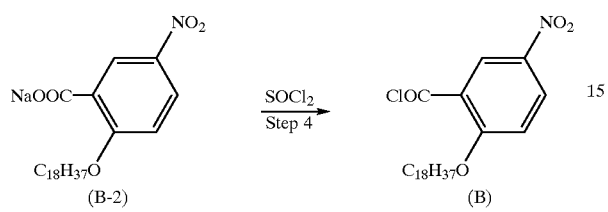
Synthesis of intermediate C
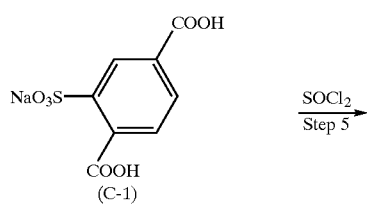
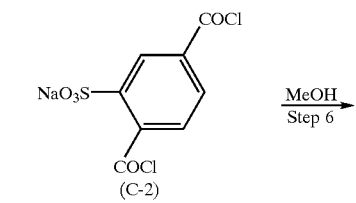
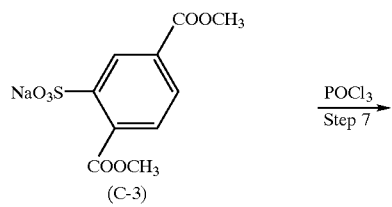
Synthesis of exemplified compound CP-1
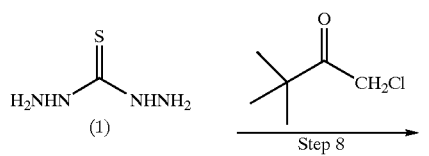
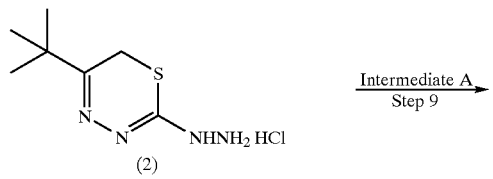
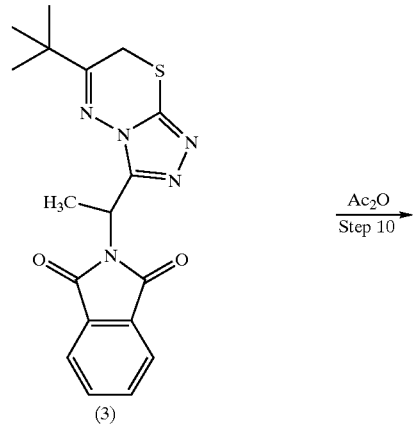
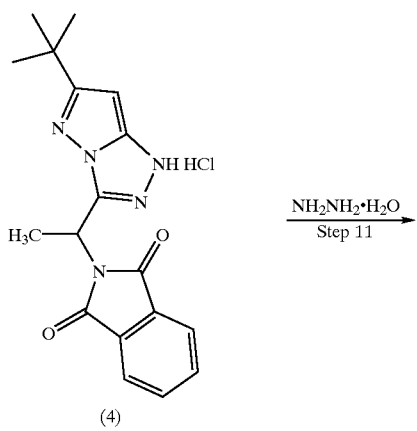
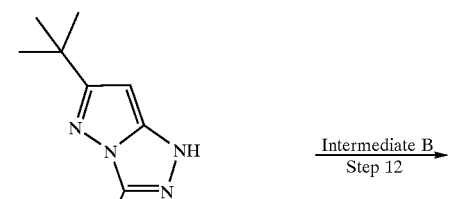
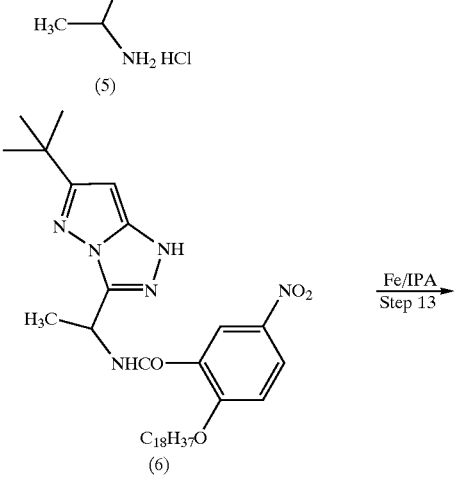

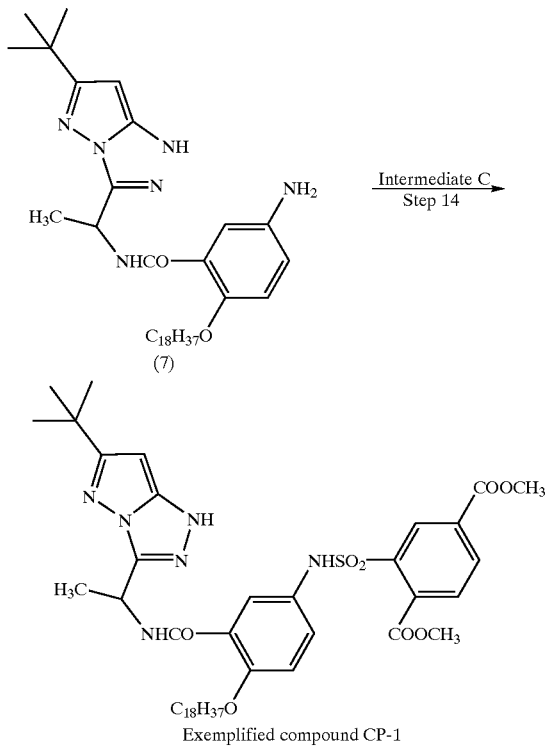

Exemplified compound CP-1

Synthesis of Intermediate (A) (Steps 1 and 2)

A mixture of 148.2 g of phthalic anhydride (A-1), 91.7 g of α-alanine (A-2), and 150 mL of acetic acid was refluxed under heating for 2 hr in an oil bath. After the reaction, the reaction solution was cooled to 60° C. and dropped into 500 mL of ice water with stirring. After that, the resultant solution was stirred at 20° C. for 1 hr, and the precipitated crystal was filtered by suction. The obtained crystal was washed with 500 mL of water and dried at 50° C. to obtain a white crystal weighing 208.3 g of an intermediate (A-3).

0.5 mL of dimethylformamide and 150 mL of toluene were added to 150 g of this intermediate (A-3), and the resultant solution was heated to 70° C. under stirring. 74.5 g of thionyl chloride were dropped into the reaction solution over 1 hr, and the solution was allowed to further react for 1 hr. After that, the solvent was distilled off by reduced-pressure concentration to obtain oily matter of an intermediate (A) weighing 162.5 g.

Synthesis of Intermediate (B) (Steps 3 and 4)

A mixture of 20.2 g of t-butoxy sodium, 54.1 g of octadecyl alcohol, and 300 mL of toluene was refluxed under heating at 130° C. After the mixture was allowed to react for 3 hr, 150 mL of the refluxing solvent were distilled off at normal pressure. The reaction solution was cooled to 70° C., and 45 g of sodium 2-chloro-5-nitrobenzoate (B-1) were added. Subsequently, 150 mL of dimethylformamide were gradually added. After being stirred for 30 min, the resultant solution was made to react at 80° C. for 1 hr. 300 mL of ethyl acetate were added, and the resultant solution was neutralized by hydrochloric acid and washed twice with 150 mL of water. The organic layer was dried with anhydrous magnesium sulfate and concentrated, and the obtained coarse oily matter was dissolved in acetonitrile. The precipitated crystal was filtered out to obtain an intermediate (B-2) weighing 70.6 g.

A mixture of 43.6 g of (B-2) thus obtained, 200 mL of acetonitrile, and 17.9 of thionyl chloride was refluxed under heating at 80° C. for 2 hr. The reaction solution was concentrated to obtain oily matter of an acid chloride intermediate (B) weighing 91 g.

Synthesis of Intermediate (C) (Steps 5, 6, and 7)

A mixture of 26.8 g of monosodium 2-sulfotelephthalate (C-1), 100 mL of toluene, 10 mL of acetonitrile, and 5 mL of dimethylformamide was stirred under heating at 95° C. on an oil bath. 25 g of thionyl chloride were dropped into the mixture over 1 hr. After the resultant solution was further allowed to react for 1 hr, toluene and excess thionyl chloride were removed by reduced-pressure concentration to obtain oily matter of an intermediate (C-2). This oily matter was dissolved in 40 mL of acetonitrile, and 100 mL of methanol were dropped at 20° C. The reaction solution was concentrated, and the precipitated crystal was dispersed in 50 mL of acetonitrile and filtered out to obtain an intermediate (C-3) weighing 24.8 g.

A mixture of the crystal of (C-3) thus obtained, 100 mL of acetonitrile, and 25.7 g of phosphorus oxychloride was allowed to react at 70° C. for 1 hr. 300 mL of ethyl acetate were added, and the resultant solution was washed twice with 150 mL of water. The organic layer was dried with anhydrous magnesium sulfate and concentrated. The obtained coarse oily matter was dissolved in hexane/ethyl acetate, and the precipitated crystal was filtered out to obtain an intermediate (C) weighting 22 g. The yield was 75.1%.

Synthesis of Intermediate (2) (Step 8)

141.4 g of 1-chloropinacolone were dropped into a mixture of 106.1 g of thiocarbohydrazide (1) and 500 mL of methyl alcohol under water cooling at 15° C. over 45 min. The water bath was removed, and the solution was allowed to further react for 2 hr and refluxed under heating for 3 hr. Subsequently, the solvent was distilled off under reduced pressure. 500 mL of acetonitrile were added to the concentrated oily matter, and the precipitated crystal was filtered by suction and washed with 150 mL of cold acetonitrile to obtain an intermediate (2) weighing 179.2 g. The yield was 80.4%.

Synthesis of Intermediate (3) (Step 9)

A mixture of 111.4 g of the intermediate (2) and 350 mL of acetonitrile was refluxed under heating. A solution containing 123.4 g of the intermediate (A) and 120 mL of acetonitrile was dropped into the mixture over 2.5 hr. After the resultant solution was further refluxed under heating for 7 hr, the reaction solution was cooled and stirred at 10° C. or less for 1 hr. The precipitated crystal was filtered by suction and washed with 100 mL of cold acetonitrile to obtain hydrochloride of an intermediate (3) weighing 151.5 g. This hydrochloride was dispersed in 350 mL of water, and a solution of 14.6 g of sodium hydroxide/12 mL of water was dropped into the dispersion at 40° C. over 30 min. The resultant solution was cooled after being stirred for 1 hr, and the precipitated crystal was filtered by suction and washed with 200 mL of water to obtain a free form of the intermediate (3) weighing 128.2 g.

Synthesis of Intermediate (4) (Step 10)

A mixture of 123.2 g of the intermediate (3) and 300 mL of acetic anhydride was stirred by reflux under heating for 5 hr. After the reaction solvent was distilled off under reduced pressure by an aspirator, 335 mL of acetonitrile and 17 mL of methanol were dropped in this order and dissolved by reflux under heating. 57.4 mL of hydrochloric acid were dropped over 30 min, and the solution was further refluxed under heating for 2 hr. The reaction solution was cooled and stirred at 10° C. or less for 1 hr. The precipitated crystal was filtered by suction and washed with 100 mL of cold acetonitrile to obtain a compound (4) weighing 128 g. The purity of the obtained intermediate (4) was 93% (HPLC). This intermediate contained sulfur produced during ring condensation as an impurity.

Synthesis of Intermediate (5) (Step 11)

56.1 g of the intermediate (4) were dispersed in 200 mL of $H_2O$, and the dispersion was heated to 40 to 50° C. A solution of 5.6 g of NaOH/10 mL of $H_2O$ was dropped over 10 min. Subsequently, a solution of 1.7 g of $NaHCO_3$/3 mL of $H_2O$ was dropped.

After the resultant solution was stirred for 30 min, the reaction solution was filtered by suction and washed with 200 mL of water. A free form of compound (4) thus obtained was dispersed in 100 mL of isopropyl alcohol, and the dispersion was stirred and refluxed under heating. 18.8 g of hydrazine monohydrate were dropped over 15 min, and the resultant solution was refluxed under heating for 1 hr. The reaction solution was cooled with water, the produced phthalhydrazide and sulfur were removed by suction filtration, and the filtrate was concentrated. The concentrated oily matter was dissolved in 300 mL of ethyl acetate, and insoluble matter was filtered off. The filtrate was cooled to 5° C. or less, and 12.2 g of hydrochloric acid gas were blown into the filtrate with stirring over 1 hr. The precipitated hydrochloride of an intermediate (5) was filtered out and washed with 50 mL of ethyl acetate, 50 mL of acetone, and 50 mL of ethyl acetate in this order to obtain a light yellow crystal (hydrochloride) of the intermediate (5) weighing 66.9 g (yield =91.5%).

Synthesis of Intermediate (6) (Step 12)

A mixture of 97.4 g of the intermediate (5), 500 mL of toluene, and 56 mL of triethylamine was stirred at room temperature, and 67.2 mL of triethylamine and a solution of 182 g of the intermediate (B)/300 mL of toluene were simultaneously dropped over 30 min. After the solution was stirred at room temperature for 1 hr, 500 mL of ethyl acetate and 300 mL of dilute hydrochloric acid were added to the reaction solution to perform extraction. The organic layer was separated and washed twice with 300 mL of water. This organic layer was dried with anhydrous magnesium sulfate and concentrated to obtain oily matter weighing 262 g. This oily matter was recrystallized by acetonitrile/ethyl acetate to obtain a crystal of an intermediate (6) weighing 95.2 g.

Synthesis of Intermediate (7) (Step 13)

A mixture of 25 g of reduced iron, 0.25 g of ammonium chloride, and 7.5 mL of water was stirred under heating in a steam bath. 0.5 mL of acetic acid was added, and the resultant solution was stirred for 5 min. After that, 125 mL of isopropyl alcohol were added, and the solution was refluxed under heating for 30 min. A solution of 25 g of the oily matter of the intermediate (6)/50 mL of isopropyl alcohol was dropped into the above solution over 30 min, and the resultant solution was further refluxed under heating for 1 hr. The reaction solution was filtered through celite, and the filtrate was concentrated. The obtained oily matter was dissolved in 50 mL of ethyl acetate and 70 mL of hexane, and insoluble matter was filtered off. When the filtrate was left to stand, a crystal precipitated. This crystal was filtered out to obtain an intermediate (7) weighing 20.2 g (yield=85.7%).

Synthesis of Exemplified Compound CP-1 (Step 14)

A mixture of 11.9 g of the intermediate (7), 150 mL of tetrahydrofuran, and 5.85 g of a compound C was stirred at room temperature, and 4.75 g of pyridine were dropped into the mixture over 5 min. After the reaction solution was stirred at room temperature for 8 hr, 200 mL of ethyl acetate was added, and the resultant solution was washed twice with 50 mL of dilute hydrochloric acid and 50 mL of water. The organic layer was dried with anhydrous magnesium sulfate and concentrated to obtain oily matter weighing 17.8 g. This coarse oily matter was purified by column chromatography by using a solvent mixture of hexane and ethyl acetate, thereby obtaining oily matter of an exemplified compound CP-1 weighing 11.8 g (yield=69.3%). The structure of this compound was confirmed by NMR and an MS spectrum.

Synthesis Example 2

(Synthesis of Exemplified Compound CP-2)

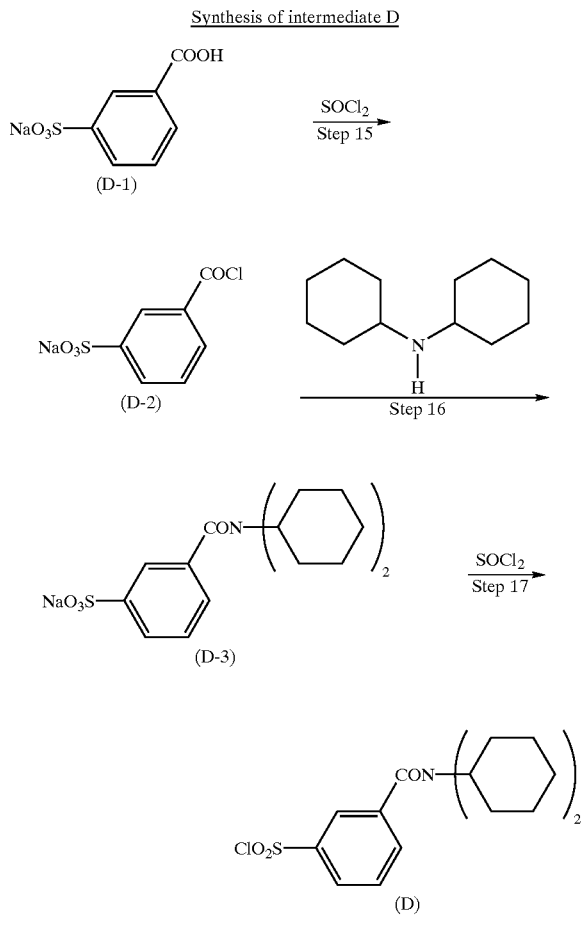

Synthesis of intermediate D

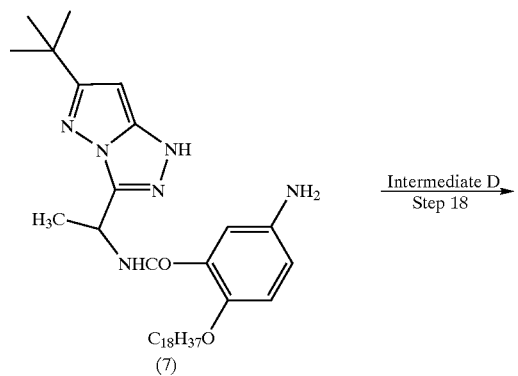

Synthesis of exemplified compound CP-2

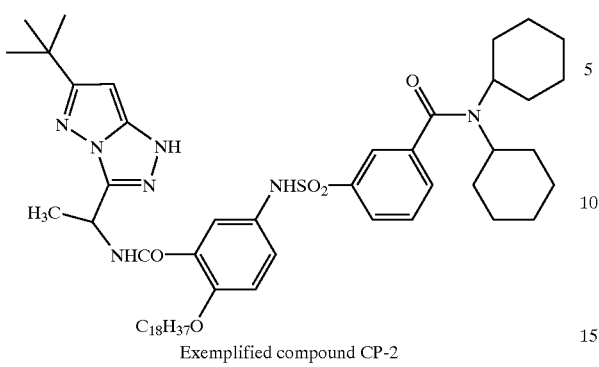

Exemplified compound CP-2

Synthesis of Intermediate (D) (Steps 15, 16, and 17)

A mixture of 71.7 g of monosodium 3-sulfobenzoate (D-1), 300 mL of toluene, 3 mL of dimethylacetamide, and 28.0 mL of thionyl chloride was stirred on an oil bath under heating at 80° C. for 4 hr. Toluene and excess thionyl chloride were distilled off at reduced pressure. 50 mL of toluene were added to perform azeotropic distillation twice, thereby obtaining oily matter of an intermediate (D-2).

A mixture of 58.0 g of dicyclohexylamine, 300 mL of tetrahydrofuran, and 53.5 g of triethylamine was stirred at 0° C., and the oily matter of the intermediate (D-2) was separately added by a small amount at a time. After that, the resultant material was allowed to react at room temperature for 2 hr, and 600 mL of ethyl acetate and 300 mL of dilute hydrochloric acid were added to separate the organic layer. This organic layer was washed twice with 200 mL of water, dried with anhydrous magnesium sulfate, and concentrated to obtain a precipitated crystal of an intermediate (D-3) weighing 70.1 g.

A mixture of 50.0 g of the intermediate (D-3), 200 mL of toluene, 3 mL of dimethylacetamide, and 38.4 g of thionyl chloride was stirred at 80° C. for 4 hr. After the reaction solution was cooled, 200 mL of ethyl acetate and 100 mL of water were added to perform extraction, and the resultant solution was further washed twice with 100 mL of water. The organic layer was dried with anhydrous magnesium sulfate and concentrated to obtain coarse oily matter weighing 43.6 g. This coarse oily matter was purified by column chromatography by using a solvent mixture of hexane and ethyl acetate, thereby obtaining oily matter of an intermediate (D) weighing 25.7 g.

Synthesis of Exemplified Compound CP-2 (Step 18)

A mixture of 7.98 g of a compound (7), 150 mL of acetonitrile, 2.17 mL of pyridine, and 5.15 g of the intermediate (D) was stirred at 70° C. for 30 min. The reaction solution was extracted by adding 200 mL of ethyl acetate and 75 mL of dilute hydrochloric acid water, and the resultant solution was further washed twice with 75 mL of water. The organic layer was dried with anhydrous magnesium sulfate and concentrated to obtain coarse oily matter weighing 12.5 g. This coarse oily matter was purified by column chromatography by using a solvent mixture of hexane and ethyl acetate, thereby obtaining oily matter of the intermediate (D) weighing 25.7 g. The structure of this compound was confirmed by NMR and an MS spectrum.

Synthesis Example 3
(Synthesis of Exemplified Compound CP-3)

Synthesis of intermediate E

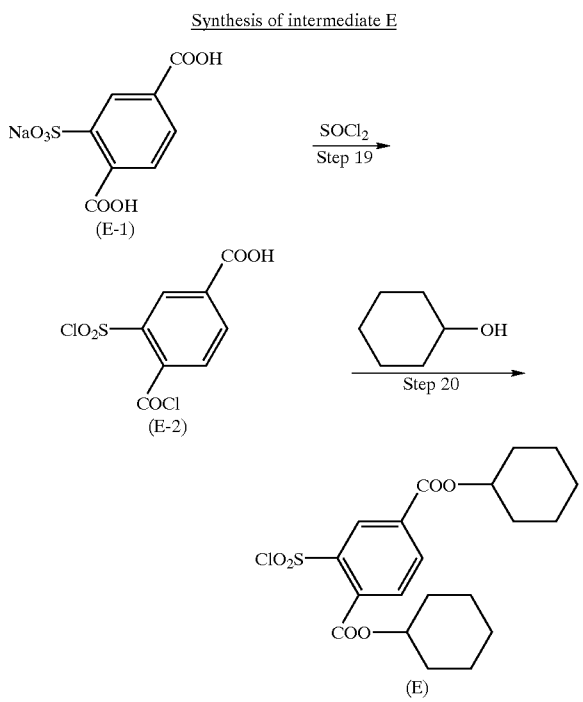

Synthesis of exemplified compound CP-3

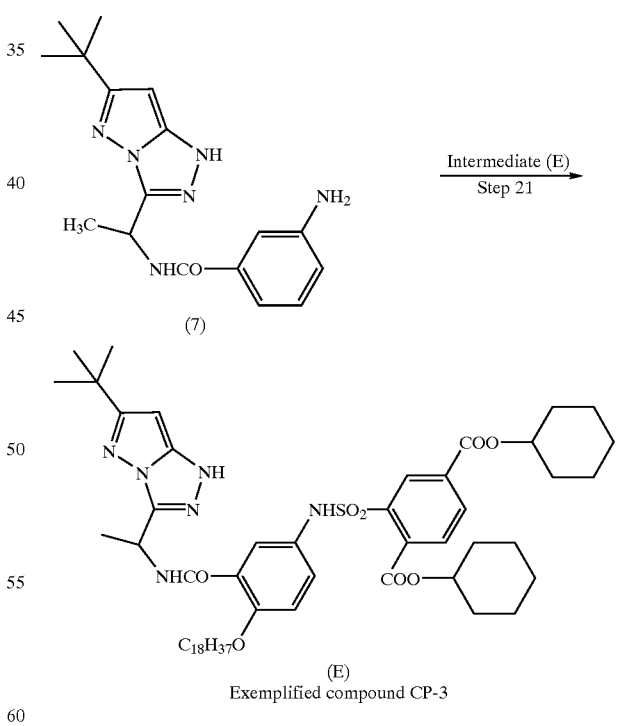

Exemplified compound CP-3

Synthesis of Intermediate (E) (Steps 19 and 20)

A mixture of 26.8 g of monosodium 2-sulfotelephthalate (E-1), 100 mL of toluene, 32.9 mL of thionyl chloride, and 0.7 mL of dimethylformamide was stirred at 90° C. for 6 hr. Subsequently, the reaction solution was concentrated at reduced pressure. 100 mL of toluene were added to dissolve the concentrated matter, and the reaction solution was cooled in an ice/acetone bath. 21 g of cyclohexanol were added to the solution, and 28 mL of triethylamine were slowly dropped while the internal temperature was held at 5° C. or less. After that, the resultant solution was stirred at 5° C. for 2 hr and at room temperature for 10 hr. 200 mL of ethyl acetate were added to the reaction solution, and the resultant solution was washed with 200 mL of water. The solution was further washed twice with 200 mL of saturated salt solution, and the organic layer was dried with anhydrous sodium sulfate. This solution was filtered out and concentrated at reduced pressure to obtain oily matter of an intermediate (E) weighing 39.5 g.

Synthesis of Exemplified Compound CP-3 (Step 21)

A mixture of 11.9 g of the intermediate (7), 150 mL of ethyl acetate, and 3.4 mL of triethylamine was stirred at room temperature, and 9.44 g of the intermediate (E) were dropped over 10 min. After that, the resultant solution was heated to 40° C. and made to react for 2 hr. After the reaction solution was cooled, 50 mL of ethyl acetate and 75 mL of dilute hydrochloric acid were added to perform extraction. The resultant solution was further washed twice with 75 mL of water. The organic layer was dried with anhydrous magnesium sulfate and concentrated to obtain coarse oily matter weighing 24.8 g. This coarse oily matter was purified by column chromatography by using a solvent mixture of hexane and ethyl acetate, thereby obtaining oily matter weighing 12.3 g. The oily matter was crystallized by a solvent mixture of acetonitrile and ethyl acetate, obtaining a crystal of an exemplified compound CP-3 weighing 9.8 g (yield=49.6%, melting point=149 to 151° C.). The structure of this compound was confirmed by NMR and an MS spectrum.

The content of coupler represented by formula (M-1), (M-2), or (M-3) of the present invention in a lightsensitive material is suitably 0.01 to 10 g, preferably 0.1 g to 2 g per m$^2$. The content is suitably $1\times10^{-3}$ to 1 mol, preferably $2\times10^{-3}$ to $3\times10^{-1}$ mol per mol of a silver halide in the same photosensitive emulsion layer.

When a photosensitive layer has a unit configuration including two or more photosensitive emulsion layers differing in sensitivity, the content of coupler of the present invention per mol of a silver halide is preferably $2\times10^{-3}$ to $2\times10^{-1}$ mol in low-speed layers, and preferably $3\times10^{-2}$ to $3\times10^{-1}$ mol in layers other than low-speed layers.

The present invention contains coupler represented by formula (M-1), (M-2), or (M-3). Although these couplers can also be used together with other couplers, the higher the contribution of color dyes of couplers of the present invention to the total density of dyes which form substantially the same color, the more favorable the obtained results. More specifically, the amount of couplers of the present invention is favorably such that the contribution to the color density is preferably 30% or more, more preferably 50% or more, and most preferably 70% or more.

The coupler represented by formula (M-1), (M-2), or (M-3) of the present invention can be introduced to a sensitive material by various known dispersion methods. Of these methods, an oil-in-water dispersion method is preferable in which a coupler is dissolved in a high-boiling organic solvent (used in combination with a low-boiling solvent where necessary), the solution is dispersed by emulsification in an aqueous gelatin solution, and the dispersion is added to a silver halide emulsion.

Examples of the high-boiling solvent used in this oil-in-water dispersion method are described in, e.g., U.S. Pat. No. 2,322,027, the disclosure of which is incorporated herein by reference. Practical examples of steps, effects, and impregnating latexes of a latex dispersion method as one polymer dispersion method are described in, e.g., U.S. Pat. No. 4,199,363, West German Patent Application (OLS) Nos. 2,541,274 and 2,541,230, Jpn. Pat. Appln. KOKOKU Publication No. (hereinafter referred to as JP-B-) 53-41091, and EP 029104, the disclosures of which are incorporated herein by reference. Dispersion using an organic solvent-soluble polymer is described in PCT International Publication WO88/00723, the disclosure of which is incorporated herein by reference.

Examples of the high-boiling solvent usable in the above-mentioned oil-in-water dispersion method are phthalic acid esters (e.g., dibutylphthalate, dioctylphthalate, dicyclohexylphthalate, bis(2-ethylhexyl)phthalate, decylphthalate, bis(2,4-di-tert-amylphenyl)isophthalate, and bis(1,1-diethylpropyl)phthalate), esters of phosphoric acid and phosphonic acid (e.g., diphenylphosphate, triphenylphosphate, tricresylphosphate, 2-ethylhexyldiphenylphosphate, dioctylbutylphosphate, tricyclohexylphosphate, tri-2-ethylhexylphosphate, tridodecylphosphate, and bis(2-ethylhexyl)phenylphosphate), benzoic acid esters (e.g., 2-ethylhexylbenzoate, 2,4-dichlorobenzoate, dodecylbenzoate, and 2-ethylhexyl-p-hydroxybenzoate), amides (e.g., N,N-diethyldodecaneamide, N,N-diethyllaurylamide, and N,N,N,N-tetrakis(2-ethylhexyl) isophthalic acid amide), alcohols and phenols (e.g., isostearylalcohol and 2,4-di-tert-amylphenol), aliphatic esters (e.g., dibutoxyethyl succinate, bis(2-ethylhexyl) succinate, 2-hexyldecyl tetradecanate, tributyl citrate, diethyl azelate, isostearyl lactate, and trioctyl tosylate), aniline derivatives (e.g., N,N-dibutyl-2-butoxy-5-tert-octylaniline), chlorinated paraffins (paraffins containing 10% to 80% of chlorine), trimesic acid esters (e.g., trimesic acid tributyl), dodecylbenzene, diisopropylnaphthalene, phenols (e.g., 2,4-di-tert-amylphenol, 4-dodecyloxyphenol, 4-dodecyloxycarbonylphenol, and 4-(4-dodecyloxyphenylsulfonyl)phenol), carboxylic acids (e.g., 2-(2,4-di-tert-amylphenoxy) butyric acid and 2-ethoxyoctanedecanic acid), alkylphosphoric acids (e.g., bis(2-ethylhexyl)phosphoric acid and diphenylphosphoric acid). In addition to the above high-boiling solvents, compounds described in, e.g., JP-A-6-258803, the disclosure of which is incorporated herein by reference, can also be preferably used as high-boiling solvents.

Of these compounds, phosphoric acid esters, amides, and aliphatic esters are preferable, and the combination of phosphoric acid esters, amides, or aliphatic esters with alcohols or phenols is also preferable.

In the present invention, the weight ratio of a high-boiling organic solvent to the coupler represented by formula (M-1), (M-2), or (M-3) is preferably 0 to 2.0, more preferably, 0 to 1.0, and most preferably, 0 to 0.4.

As a co-solvent, it is also possible to use an organic solvent having a boiling point of 30° C. to about 160° C. (e.g., ethyl acetate, butyl acetate, ethyl propionate, methylethylketone, cyclohexanone, 2-ethoxyethylacetate, and dimethylformamide).

A sensitive material of the present invention can also contain a competing compound (a compound which competes with an image forming coupler to react with an oxidized form of a color developing agent and which does not form any dye image). Examples of this competing coupler are reducing compounds such as hydroquinones, catechols, hydrazines, and sulfonamidophenols, and compounds which couple with an oxidized form of a color developing agent but do not substantially form a color image (e.g., colorless compound-forming couplers disclosed in German Patent No. 1,155,675, British Patent No. 861,138, and U.S. Pat. Nos. 3,876,428 and 3,912,513, and flow-out couplers disclosed in JP-A-6-83002, the disclosures of which are incorporated herein by reference).

The competing compound is preferably added to a sensitive emulsion layer containing a magenta coupler represented by formula (M-1), (M-2), or (M-3) of the present invention or a non-sensitive layer. The completing compound is particularly preferably added to a sensitive emulsion layer containing a coupler of the present invention. The addition content of the competing compound is 0.01 to 10 g, preferably 0.10 to 5.0 g per m$^2$ of a sensitive material. The content is 1 to 1,000 mol %, preferably 20 to 500 mol % with respect to the coupler of the present invention.

In a sensitive material of the present invention, a sensitive unit sensitive to the same color can have a non-color-forming interlayer. Additionally, this interlayer preferably contains a compound selectable as the aforementioned competing compound.

To prevent deterioration of the photographic properties caused by formaldehyde gas, the sensitive material of the present invention preferably contains a compound described in U.S. Pat. No. 4,411,987 or 4,435,503, which can react with and fix formaldehyde gas, the disclosure of which is incorporated herein by reference.

A lightsensitive material of the present invention preferably have at least one blue-sensitive silver halide emulsion layer, at least one green-sensitive silver halide emulsion layer, and at least one red-sensitive silver halide emulsion layer on a support. These layers are preferably formed by coating in this order from the one farthest from the support, but different orders can also be used. In the present invention, red-, green-, and blue-sensitive silver halide emulsion layers are preferably formed in this order by coating from the one closest to the support. Also, each color-sensitive layer preferably has a unit configuration including two or more photosensitive emulsion layers differing in sensitivity. In particular, a three-layered unit configuration including three photosensitive emulsion layers, i.e., low-, medium-, and high-speed layers in this order from the one closest to the support is favored.

One preferred embodiment of the present invention is a photosensitive element in which a support is coated with layers in the order of an undercoat layer/antihalation layer/ first interlayer/red-sensitive emulsion layer unit (including three layers in the order of a low-speed red-sensitive layer/ medium-speed red-sensitive layer/high-speed red-sensitive layer from the one closest to the support)/second interlayer/ green-sensitive emulsion layer unit (including three layers in the order of a low-speed green-sensitive layer/medium-speed green-sensitive layer/high-speed green-sensitive layer from the one closest to the support)/third interlayer/yellow filter layer/blue-sensitive emulsion layer unit (including three layers in the order of a low-speed blue-sensitive layer/medium-speed blue-sensitive layer/high-speed blue-sensitive layer from the one closest to the support)/first protective layer/second protective layer.

Each of the first, second, and third interlayers can be a single layer or two or more layers. The first interlayer is preferably divided into two or more layers, and the layer directly adjacent to the red-sensitive layer preferably contains yellow colloidal silver.

Likewise, the second interlayer preferably includes two or more layers, and the layer directly adjacent to the green-sensitive layer preferably contains yellow colloidal silver.

In addition, a fourth interlayer is preferably formed between the yellow filter layer and the blue-sensitive emulsion layer unit.

Also, the protective layer preferably has a three-layered configuration including first to third protective layers. When the protective layer includes two or three layers, the second protective layer preferably contains a fine-grain silver halide having an average equivalent-sphere grain size of 0.10 μm or less. This silver halide is preferably silver bromide or silver iodobromide.

Coupler represented by formula (M-1), (M-2), or (M-3) of the present invention are preferably added to a green-sensitive layer. When the green-sensitive layer is made up of a plurality of photosensitive emulsion layers different in sensitivity, the coupler of the present invention are preferably added to at least the lowest-speed emulsion layer.

In silver halide photosensitive materials of the present invention and silver halide photographic emulsions used therein, it is generally possible to use various techniques and inorganic and organic materials described in Research Disclosure Nos. 308119 (1989), 37038 (1995), and 40145 (1997), the disclosures of which are incorporated herein by reference.

In addition, techniques and inorganic and organic materials usable in color photosensitive materials of the present invention can be applied are described in portions of EP436, 938A2 and patents cited below, the disclosures of which are incorporated herein by reference.

|    | Items | Corresponding portions |
|----|-------|------------------------|
| 1) | Layer configurations | page 146, line 34 to page 147, line 25 |
| 2) | Silver halide emulsions usable together | page 147, line 26 to page 148 line 12 |
| 3) | Yellow couplers usable together | page 137, line 35 to page 146, line 33, and page 149, lines 21 to 23 |
| 4) | Magenta couplers usable together | page 149, lines 24 to 28; EP421,453A1, page 3, line 5 to page 25, line 55 |
| 5) | Cyan couplers usable together | page 149, lines 29 to 33; EP432,804A2, page 3, line 28 to page 40, line 2 |
| 6) | Polymer couplers | page 149, lines 34 to 38; EP435,334A2, page 113, line 39 to page 123, line 37 |
| 7) | Colored couplers | page 53, line 42 to page 137, line 34, and page 149, lines 39 to 45 |
| 8) | Functional couplers usable together | page 7, line 1 to page 53, line 41, and page 149, line 46 to page 150, line 3; EP435,334A2, page 3, line 1 to page 29, line 50 |
| 9) | Antiseptic and mildewproofing agents | page 150, lines 25 to 28 |
| 10) | Formalin scavengers | page 149, lines 15 to 17 |
| 11) | Other additives usable together | page 153, lines 38 to 47; EP421,453A1, page 75, line 21 to page 84, line 56, and page 27, line 40 to page 37, line 40 |
| 12) | Dispersion methods | page 150, lines 4 to 24 |
| 13) | Supports | page 150, lines 32 to 34 |
| 14) | Film thickness. film physical properties | page 150, lines 35 to 49 |
| 15) | Color development step | page 150, line 50 to page 151, line 47 |
| 16) | Desilvering step | page 151, line 48 to page 152, line 53 |

-continued

| Items | | Corresponding portions |
|---|---|---|
| 17) | Automatic processor | page 152, line 54 to page 153, line 2 |
| 18) | Washing.stabilizing step | page 153, lines 3 to 37 |

EXAMPLE-1

The present invention will be described in more detail below by way of its examples. However, the invention is not limited to these examples. Making of sample 101.

Sample 101 was made by coating photosensitive emulsion layers presented below on a 127-μm thick undercoated cellulose triacetate support. The numbers represent the addition amounts per m².

The effects of added compounds are not restricted to the described purposes.

1st layer: Antihalation layer

| | | |
|---|---|---|
| Black colloidal silver | | 0.30 g |
| Gelatin | | 3.00 g |
| Ultraviolet absorbent U-1 | | 0.05 g |
| Ultraviolet absorbent U-3 | | 0.10 g |
| Ultraviolet absorbent U-4 | | 0.05 g |
| High-boiling organic solvent Oil-1 | | 0.20 g |
| High-boiling organic solvent Oil-2 | | 0.20 g |
| High-boiling organic solvent Oil-5 | | 0.010 g |
| Dye D-4 | | 1.0 mg |
| Dye D-8 | | 1.5 mg |
| Fine-crystal solid dispersion of dye E-1 | | 0.05 g |

2nd layer: Interlayer

| | | |
|---|---|---|
| Gelatin | | 0.40 g |
| Compound Cpd-A | | 0.2 mg |
| Compound Cpd-K | | 2.0 mg |
| Compound Cpd-M | | 0.030 g |
| Ultraviolet absorbent U-6 | | 4.0 mg |
| High-boiling organic solvent Oil-3 | | 0.010 g |
| High-boiling organic solvent Oil-4 | | 0.010 g |
| High-boiling organic solvent Oil-7 | | 2.0 mg |
| Dye D-7 | | 3.0 mg |

3rd layer: Photosensitive emulsion layer

| | | |
|---|---|---|
| Emulsion R | silver | 0.5 g |
| Fine-grain silver iodide emulsion (cubic, average equivalent-sphere grain size 0.05 μm) | silver | 0.020 g |
| Gelatin | | 1.0 g |
| Compound Cpd-M | | 0.20 g |
| Compound Cpd-K | | 2.0 mg |
| High-boiling organic solvent Oil-6 | | 0.10 g |
| Ultraviolet absorbent U-1 | | 0.10 g |

4th layer: Interlayer

| | | |
|---|---|---|
| Gelatin | | 0.6 g |
| Compound Cpd-M | | 0.080 g |
| High-boiling organic solvent Oil-6 | | 0.050 g |

5th layer: Interlayer

| | | |
|---|---|---|
| Yellow colloidal silver | | 0.010 g |
| Gelatin | | 0.60 g |
| Compound Cpd-D | | 0.020 g |
| High-boiling organic solvent Oil-3 | | 0.010 g |

6th layer: Low-speed red-sensitive emulsion layer

| | | |
|---|---|---|
| Emulsion A | silver | 0.25 g |
| Emulsion B | silver | 0.25 g |
| Gelatin | | 0.80 g |
| Coupler C-1 | | 0.040 g |

-continued

| | | |
|---|---|---|
| Coupler C-2 | | 0.070 g |
| Coupler C-9 | | 5.0 mg |
| Coupler C-11 | | 0.020 g |
| Ultraviolet absorbent U-3 | | 0.010 g |
| Compound Cpd-A | | 1.0 mg |
| Compound Cpd-I | | 0.020 g |
| Compound Cpd-J | | 2.0 mg |
| High-boiling organic solvent Oil-2 | | 0.050 g |
| Additive P-1 | | 0.020 g |

7th layer: Medium-speed red-sensitive emulsion layer

| | | |
|---|---|---|
| Emulsion C | silver | 0.20 g |
| Emulsion D | silver | 0.25 g |
| Gelatin | | 0.80 g |
| Coupler C-1 | | 0.12 g |
| Coupler C-2 | | 0.050 g |
| Coupler C-3 | | 0.010 g |
| Coupler C-11 | | 0.030 g |
| Ultraviolet absorbent U-3 | | 0.010 g |
| High-boiling organic solvent Oil-2 | | 0.070 g |
| Additive P-1 | | 0.020 g |

8th layer: High-speed red-sensitive emulsion layer

| | | |
|---|---|---|
| Emulsion E | silver | 0.20 g |
| Emulsion F | silver | 0.25 g |
| Gelatin | | 1.50 g |
| Coupler C-1 | | 0.020 g |
| Coupler C-2 | | 0.010 g |
| Coupler C-3 | | 0.60 g |
| Coupler C-6 | | 0.010 g |
| Coupler C-11 | | 0.20 g |
| Ultraviolet absorbent U-1 | | 0.010 g |
| Ultraviolet absorbent U-2 | | 0.010 g |
| High-boiling organic solvent Oil-2 | | 0.030 g |
| High-boiling organic solvent Oil-9 | | 0.010 g |
| Compound Cpd-D | | 5.0 mg |
| Compound Cpd-L | | 1.0 mg |
| Compound Cpd-F | | 0.030 g |
| Additive P-1 | | 0.10 g |

9th layer: Interlayer

| | | |
|---|---|---|
| Gelatin | | 0.50 g |
| Compound Cpd-I | | 0.010 g |
| Dye D-5 | | 0.020 g |
| Dye D-9 | | 3.0 mg |
| Compound Cpd-M | | 0.10 g |
| Compound Cpd-O | | 3.0 mg |
| Compound Cpd-P | | 5.0 mg |
| High-boiling organic solvent Oil-6 | | 0.050 g |

10th layer: Interlayer

| | | |
|---|---|---|
| Yellow colloidal silver | silver | 0.020 g |
| Gelatin | | 1.70 g |
| Additive P-2 | | 0.05 g |
| Ultraviolet absorbent U-1 | | 0.010 g |
| Ultraviolet absorbent U-3 | | 0.010 g |
| Compound Cpd-A | | 0.050 g |
| Compound Cpd-D | | 0.030 g |
| Compound Cpd-F | | 6.0 mg |
| Compound Cpd-M | | 0.10 g |
| High-boiling organic solvent Oil-3 | | 0.010 g |
| High-boiling organic solvent Oil-6 | | 0.10 g |

11th layer: Low-speed green-sensitive emulsion layer

| | | |
|---|---|---|
| Emulsion G | silver | 0.20 g |
| Emulsion H | silver | 0.35 g |
| Emulsion I | silver | 0.20 g |
| Gelatin | | 1.70 g |
| Coupler C-7 | | 0.13 g |
| Coupler C-8 | | 0.12 g |
| Compound Cpd-B | | 0.030 g |
| Compound Cpd-D | | 5.0 mg |
| Compound Cpd-E | | 5.0 mg |
| Compound Cpd-G | | 2.5 mg |
| Compound Cpd-K | | 2.0 mg |
| Ultraviolet absorbent U-6 | | 5.0 mg |
| High-boiling organic solvent Oil-2 | | 0.10 g |
| High-boiling organic solvent Oil-4 | | 8.0 mg |

-continued

| 12th layer: Medium-speed green-sensitive emulsion layer | | |
|---|---|---|
| Emulsion I | silver | 0.20 g |
| Emulsion J | silver | 0.30 g |
| Silver bromide emulsion fogged only internally (cubic, average equivalent-sphere grain size 0.11 μm) | silver | 0.010 g |
| Gelatin | | 0.70 g |
| Coupler C-4 | | 0.50 g |
| Coupler C-8 | | 0.020 g |
| Compound Cpd-B | | 0.030 g |
| Compound Cpd-F | | 0.010 g |
| Compound Cpd-G | | 2.0 mg |
| High-boiling organic solvent Oil-2 | | 0.050 g |
| High-boiling organic solvent Oil-5 | | 6.0 mg |
| 13th layer: High-speed green-sensitive emulsion layer | | |
| Emulsion K | silver | 0.50 g |
| Gelatin | | 0.70 g |
| Coupler C-3 | | 5.0 mg |
| Coupler C-4 | | 0.60 g |
| Coupler C-8 | | 0.010 g |
| Compound Cpd-B | | 0.050 g |
| Compound Cpd-F | | 0.010 g |
| Compound Cpd-K | | 2.0 mg |
| High-boiling organic solvent Oil-2 | | 0.050 g |
| High-boiling organic solvent Oil-8 | | 0.010 g |
| 14th layer: Yellow filter layer | | |
| Yellow colloidal silver | silver | 0.010 g |
| Gelatin | | 1.20 g |
| Compound Cpd-C | | 0.010 g |
| Compound Cpd-M | | 0.20 g |
| High-boiling organic solvent Oil-1 | | 0.020 g |
| High-boiling organic solvent Oil-6 | | 0.10 g |
| Fine-crystal solid dispersion of dye E-2 | | 0.30 g |
| 15th layer: Interlayer | | |
| Gelatin | | 0.70 g |
| Compound Cpd-M | | 0.15 g |
| High-boiling organic solvent Oil-6 | | 0.15 g |
| Dye D-6 | | 3.0 mg |
| 16th layer: Interlayer | | |
| Fine-grain silver iodide emulsion (cubic, average equivalent-sphere grain size 0.05 μm) | silver | 0.020 g |
| Gelatin | | 0.40 g |
| Compound Cpd-Q | | 0.20 g |
| 17th layer: Low-speed blue-sensitive emulsion layer | | |
| Emulsion L | silver | 0.20 g |
| Emulsion M | silver | 0.15 g |
| Emulsion N | silver | 0.15 g |
| Gelatin | | 0.90 g |
| Coupler C-5 | | 0.020 g |
| Coupler C-6 | | 5.0 mg |
| Coupler C-10 | | 0.30 g |
| Compound Cpd-B | | 0.10 g |
| Compound Cpd-I | | 8.0 mg |
| Compound Cpd-K | | 1.0 mg |
| Compound Cpd-M | | 0.010 g |
| Ultraviolet absorbent U-6 | | 0.010 g |
| High-boiling organic solvent Oil-2 | | 0.010 g |
| 18th layer: Medium-speed blue-sensitive emulsion layer | | |
| Emulsion N | silver | 0.20 g |
| Emulsion O | silver | 0.25 g |
| Gelatin | | 0.90 g |
| Coupler C-5 | | 0.020 g |
| Coupler C-6 | | 0.010 g |
| Coupler C-10 | | 0.25 g |
| Compound Cpd-B | | 0.10 g |
| Compound Cpd-N | | 2.0 mg |
| High-boiling organic solvent Oil-2 | | 0.010 g |
| 19th layer: High-speed blue-sensitive emulsion layer | | |
| Emulsion P | silver | 0.20 g |
| Emulsion Q | silver | 0.25 g |
| Gelatin | | 2.00 g |
| Coupler C-5 | | 0.10 g |
| Coupler C-6 | | 0.020 g |
| Coupler C-10 | | 1.00 g |
| High-boiling organic solvent Oil-2 | | 0.10 g |
| High-boiling organic solvent Oil-3 | | 0.020 g |
| Ultraviolet absorbent U-6 | | 0.10 g |
| Compound Cpd-B | | 0.20 g |
| Compound Cpd-N | | 0.010 g |
| 20th layer: 1st protective layer | | |
| Gelatin | | 1.20 g |
| Ultraviolet absorbent U-1 | | 0.15 g |
| Ultraviolet absorbent U-2 | | 0.10 g |
| Ultraviolet absorbent U-5 | | 0.20 g |
| Compound Cpd-O | | 5.0 mg |
| Compound Cpd-A | | 0.030 g |
| Compound Cpd-H | | 0.20 g |
| Dye D-1 | | 8.0 mg |
| Dye D-2 | | 5.0 mg |
| Dye D-3 | | 4.0 mg |
| High-boiling organic solvent Oil-3 | | 0.10 g |
| 21st layer: 2nd protective layer | | |
| Colloidal silver | silver | 2.5 mg |
| Fine-grain silver iodobromide emulsion (average grain size 0.06 μm, AgI content 1 mol %) | silver | 0.10 g |
| Gelatin | | 0.80 g |
| Ultraviolet absorbent U-1 | | 0.030 g |
| Ultraviolet absorbent U-6 | | 0.030 g |
| High-boiling organic solvent Oil-6 | | 0.030 g |
| 22nd layer: 3rd protective layer | | |
| Gelatin | | 1.20 g |
| Polymethylmethacrylate (average grain size 1.5 μm) | | 0.10 g |
| 6:4 copolymer of methylmethacrylate and methacrylic acid (average grain size 1.5 μm) | | 0.15 g |
| Silicone oil SO-1 | | 0.30 g |
| Surfactant W-1 | | 5.0 mg |
| Surfactant W-2 | | 8.0 mg |
| Surfactant W-3 | | 0.040 g |
| Surfactant W-7 | | 0.015 g |

In addition to the above compositions, additives F-1 to F-8 were added to all emulsion layers. Also, a gelatin hardener H-1 and surfactants W-3, W-4, W-5, and W-6 for coating and emulsification were added to each layer.

Furthermore, phenol, 1,2-benzisothiazoline-3-one, 2-phenoxyethanol, phenethylalcohol, and p-benzoic butylester were added as antiseptic and mildewproofing agents.

TABLE 1

Silver iodobromide emulsions used in sample 101

| Emulsion | Characteristics | Average equivalent-sphere grain size (μm) | Variation coefficient (%) | Average AgI content (%) | Halogen composition structure of silver halide grain | AgI content (%) in grain surface | ① | ② | ③ | ④ | ⑤ |
|---|---|---|---|---|---|---|---|---|---|---|---|
| A | Monodisperse tetradecahedral grain | 0.20 | 9 | 3.5 | Triple structure | 1.5 | ○ | | | | |
| B | Monodisperse (111) tabular grain Average aspect ratio 2.0 | 0.23 | 10 | 3.5 | Triple structure | 2.5 | ○ | ○ | | ○ | ○ |
| C | Monodisperse (111) tabular grain Average aspect ratio 3.0 | 0.35 | 19 | 3.0 | Triple structure | 0.1 | ○ | ○ | | ○ | ○ |
| D | Monodisperse (111) tabular grain Average aspect ratio 3.0 | 0.38 | 15 | 2.8 | Triple structure | 1.0 | ○ | ○ | | ○ | ○ |
| E | Monodisperse (111) tabular grain Average aspect ratio 3.0 | 0.40 | 10 | 2.5 | Quadruple structure | 2.5 | ○ | | | | |
| F | Monodisperse (111) tabular grain Average aspect ratio 4.5 | 0.55 | 12 | 1.6 | Triple structure | 0.6 | ○ | ○ | | | ○ |
| G | Monodisperse cubic grain | 0.18 | 9 | 3.5 | Quadruple structure | 2.0 | | | ○ | | |
| H | Monodisperse cubic grain | 0.20 | 15 | 3.9 | Quadruple structure | 1.1 | ○ | ○ | ○ | | |

TABLE 2

Silver iodobromide emulsions used in sample 101

| Emulsion | Characteristics | Average equivalent-sphere grain size (μm) | Variation coefficient (%) | Average AgI content (%) | Halogen composition structure of silver halide grain | AgI content (%) in grain surface | ① | ② | ③ | ④ | ⑤ |
|---|---|---|---|---|---|---|---|---|---|---|---|
| I | Monodisperse (111) tabular grain Average aspect ratio 4.0 | 0.30 | 12 | 4.5 | Quintuple structure | 3.5 | ○ | ○ | | ○ | ○ |
| J | Monodisperse (111) tabular grain Average aspect ratio 5.0 | 0.45 | 21 | 3.0 | Quadruple structure | 0.5 | ○ | ○ | | ○ | ○ |
| K | Monodisperse (111) tabular grain Average aspect ratio 5.5 | 0.60 | 13 | 1.7 | Triple structure | 1.3 | ○ | ○ | | | ○ |
| L | Monodisperse tetradecahedral grain | 0.31 | 9 | 5.5 | Triple structure | 4.0 | | | | ○ | ○ |
| M | Monodisperse tetradecahedral grain | 0.31 | 9 | 3.5 | Triple structure | 3.0 | ○ | ○ | | ○ | ○ |
| N | Monodisperse (111) tabular grain Average aspect ratio 3.0 | 0.33 | 13 | 3.0 | Triple structure | 4.0 | ○ | ○ | | | |
| O | Monodisperse (111) tabular grain Average aspect ratio 3.0 | 0.43 | 9 | 3.5 | Quadruple structure | 1.5 | ○ | ○ | | ○ | ○ |

TABLE 3

Silver iodobromide emulsions used in sample 101

| Emulsion | Characteristics | Average equivalent-sphere grain size (μm) | Variation coefficient (%) | Average AgI content (%) | Halogen composition structure of silver halide grain | AgI content (%) in grain surface | ① | ② | ③ | ④ | ⑤ |
|---|---|---|---|---|---|---|---|---|---|---|---|
| P | Monodisperse (111) tabular grain Average aspect ratio 6.0 | 0.75 | 21 | 2.8 | Triple structure | 0.5 | ○ | ○ | | | ○ |
| Q | Monodisperse (111) tabular grain Average aspect ratio 6.0 | 0.90 | 8 | 2.0 | Quadruple structure | 1.5 | ○ | ○ | | | ○ |

TABLE 3-continued

Silver iodobromide emulsions used in sample 101

| Emulsion | Characteristics | Average equivalent-sphere grain size (μm) | Variation coefficient (%) | Average AgI content (%) | Halogen composition structure of silver halide grain | AgI content (%) in grain surface | Other characteristics ① ② ③ ④ ⑤ |
|---|---|---|---|---|---|---|---|
| R | Monodisperse (111) tabular grain Average aspect ratio 6.0 | 0.60 | 15 | 5.0 | Triple structure | 0.5 | ○ |

(Other characteristics)
①: Reduction sensitizers were added during grain formation.
②: Selenium sensitizers were used as after-ripening chemicals.
③: Rhodium salt was added during grain formation.
④: After after-ripening, 10% of silver nitrate as a silver molar ratio with respect to emulsion grains at that point and equimolar potassium bromide were added to form shells.
⑤: 10 or more dislocation lines were observed per grain on the average with a transmission electron microscope.
Note that all photosensitive emulsions were after-ripened by using sodium thiosulfate, potassium thiocyanate, and sodium chloroaurate.
Note also that iridium salt was appropriately added during grain formation.
Note also that chemically modified gelatin in which a portion of an amino group of gelatin was replaced with amide phthalate was added to emulsions B, C, E, H, J, N, and Q during emulsion preparation.

TABLE 4

Spectral sensitization of emulsions A–P

| Emulsion | Added sensitizing dyes | Addition amount (g) per mol of silver halide |
|---|---|---|
| A | S-1 | 0.01 |
|  | S-2 | 0.20 |
|  | S-3 | 0.02 |
|  | S-8 | 0.25 |
|  | S-13 | 0.015 |
|  | S-14 | 0.01 |
| B | S-2 | 0.20 |
|  | S-3 | 0.02 |
|  | S-8 | 0.20 |
|  | S-13 | 0.015 |
|  | S-14 | 0.01 |
| C | S-2 | 0.25 |
|  | S-3 | 0.04 |
|  | S-8 | 0.25 |
|  | S-13 | 0.02 |
|  | S-14 | 0.04 |
| D | S-2 | 0.25 |
|  | S-3 | 0.03 |
|  | S-8 | 0.25 |
|  | S-13 | 0.01 |
| E | S-1 | 0.01 |
|  | S-2 | 0.20 |
|  | S-3 | 0.05 |
|  | S-8 | 0.25 |
|  | S-13 | 0.01 |
|  | S-14 | 0.02 |
| F | S-2 | 0.20 |
|  | S-3 | 0.04 |
|  | S-8 | 0.20 |
|  | S-14 | 0.02 |
| G | S-4 | 0.3 |
|  | S-5 | 0.05 |
|  | S-12 | 0.1 |
| H | S-4 | 0.2 |
|  | S-5 | 0.05 |
|  | S-9 | 0.15 |
|  | S-14 | 0.02 |

TABLE 5

Spectral sensitization of emulsions A–P

| Emulsion | Added sensitizing dyes | Addition amount (g) per mol of silver halide |
|---|---|---|
| I | S-4 | 0.3 |
|  | S-9 | 0.2 |
|  | S-12 | 0.1 |
| J | S-4 | 0.35 |
|  | S-5 | 0.05 |
|  | S-12 | 0.1 |
| K | S-4 | 0.3 |
|  | S-9 | 0.05 |
|  | S-12 | 0.1 |
|  | S-14 | 0.02 |
| L | S-6 | 0.1 |
|  | S-10 | 0.2 |
|  | S-11 | 0.05 |
| M | S-6 | 0.05 |
|  | S-7 | 0.05 |
|  | S-10 | 0.25 |
|  | S-11 | 0.05 |
| N | S-10 | 0.4 |
|  | S-11 | 0.15 |
| O | S-6 | 0.05 |
|  | S-7 | 0.05 |
|  | S-10 | 0.3 |
|  | S-11 | 0.1 |
| P | S-6 | 0.05 |
|  | S-7 | 0.05 |
|  | S-10 | 0.2 |
|  | S-11 | 0.25 |
| Q | S-6 | 0.05 |
|  | S-7 | 0.05 |
|  | S-10 | 0.2 |
|  | S-11 | 0.25 |
| R | S-15 | 0.35 |

C-1
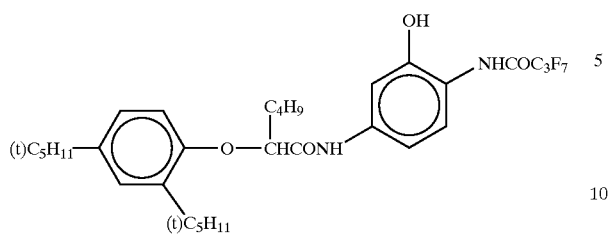
C-2
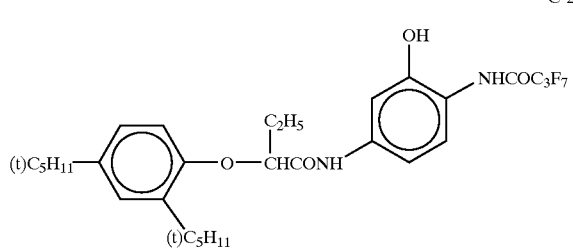
C-3
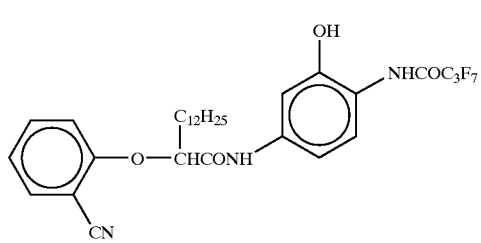
C-4
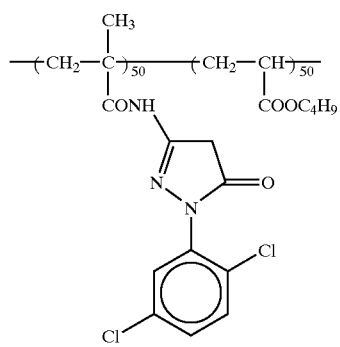
Numbers are expressed in weight %
Average molecular weight: about 25,000
C-5
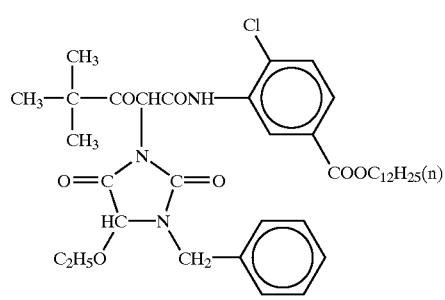
-continued
C-6
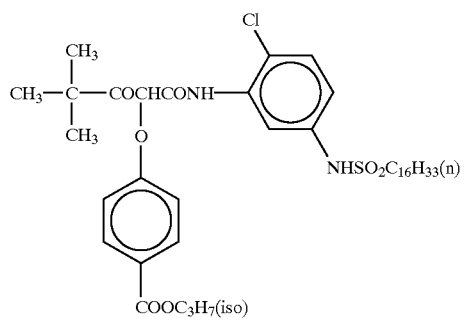
C-7
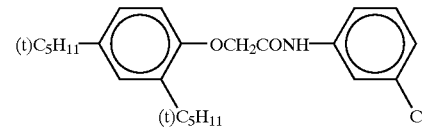
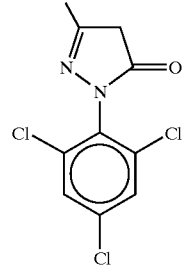
C-8
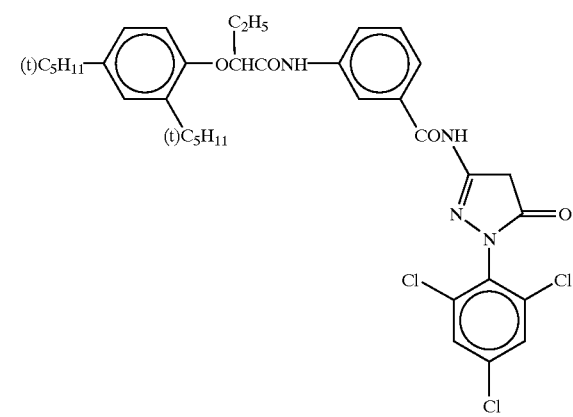
C-9
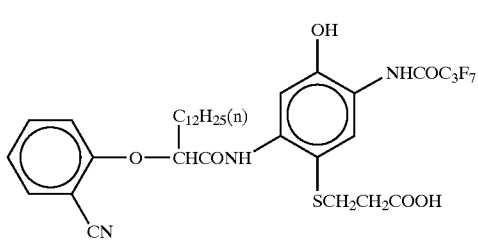

-continued

C-10

C-11

Oil-1 Tri-n-hexyl phosphate

Oil-2 Tricresyl phosphate

Oil-3

$$O=P{\left(OCH_2CH_2CH(CH_3)CH_2CH(CH_3)CH_3\right)}_3$$

Oil-4 Tricyclohexyl phosphate

Oil-5 Di-2-ethylhexyl succinate

Oil-6

Oil-7

Oil-8

-continued

Oil-9

Cpd-A

Cpd-B

Cpd-C

Cpd-D

Cpd-E

Cpd-F

Cpd-G
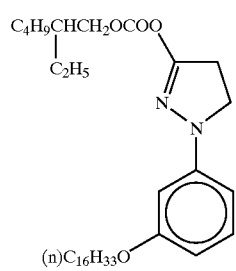
Cpd-H
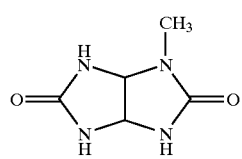
Cpd-I
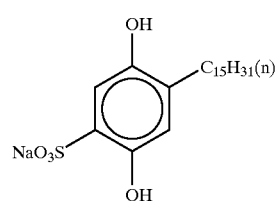
Cpd-J
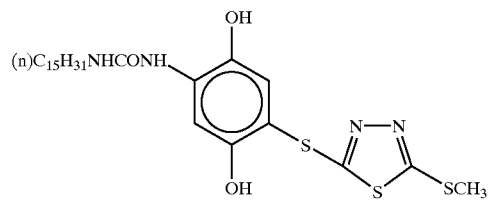
Cpd-K
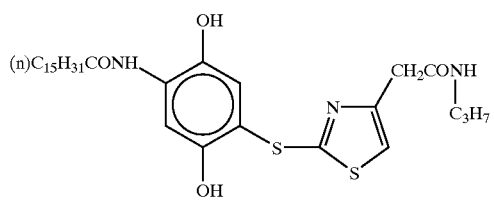
Cpd-L
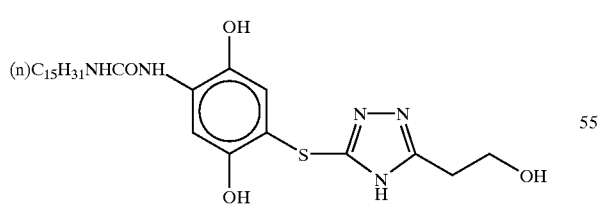
Cpd-M
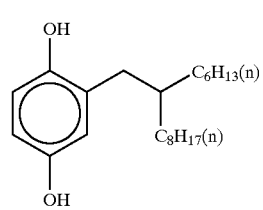
Cpd-N
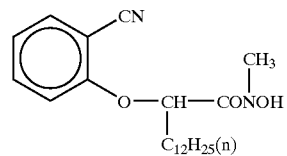
Cpd-O
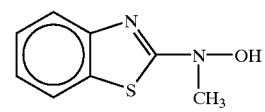
Cpd-P
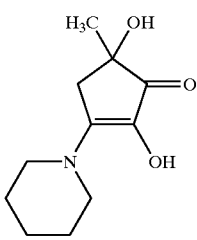
Cpd-Q
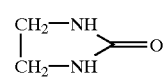
U-1
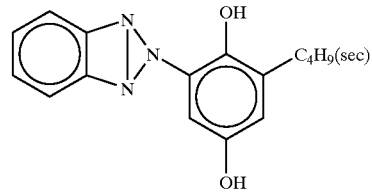
U-2
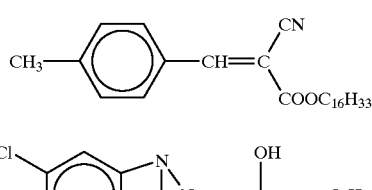
U-3
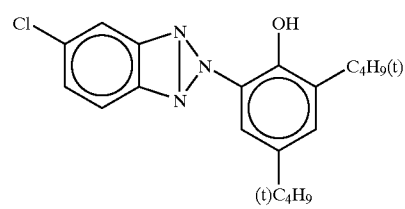
U-4
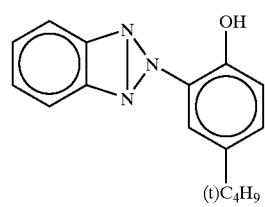
U-5
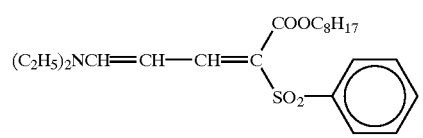

-continued
U-6
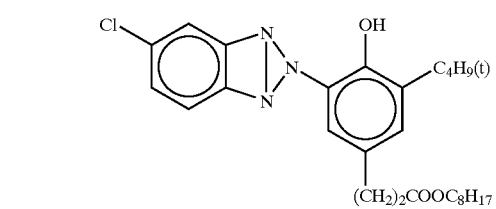
S-1
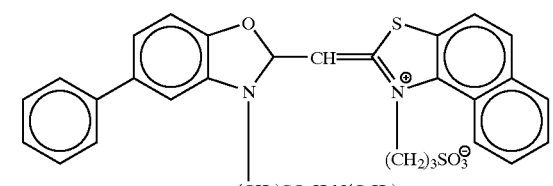
S-2
S-3
S-4
S-5
S-6
-continued
S-7
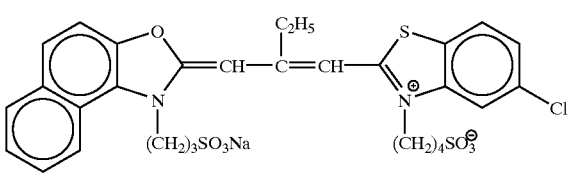
S-8
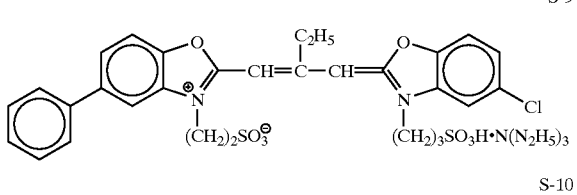
S-9
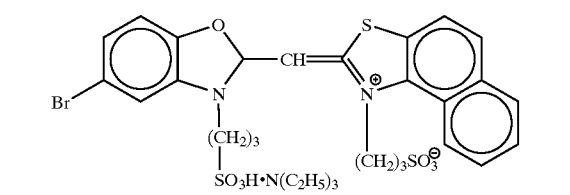
S-10
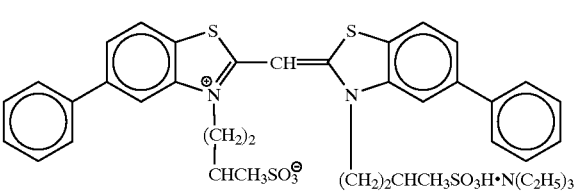
S-11
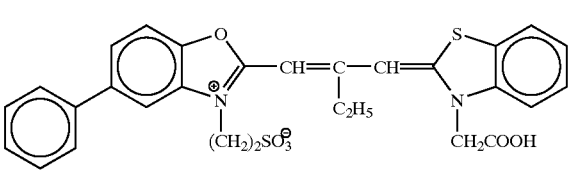
S-12
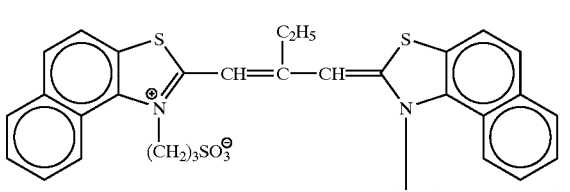
S-13
S-14
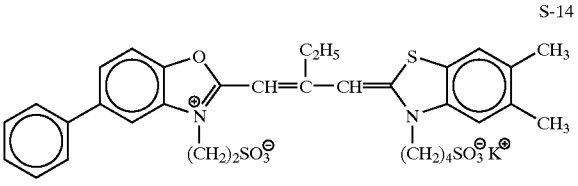

S-15
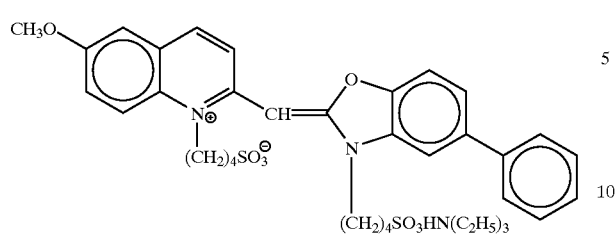
D-1
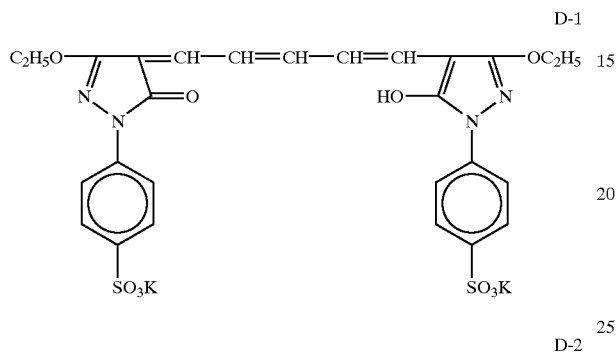
D-2
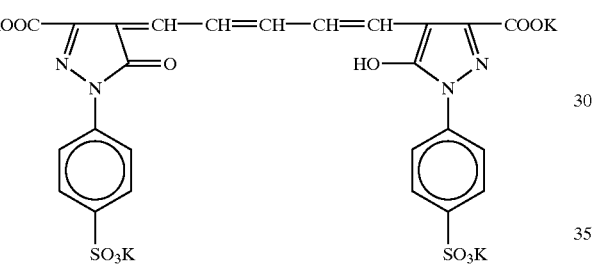
D-3
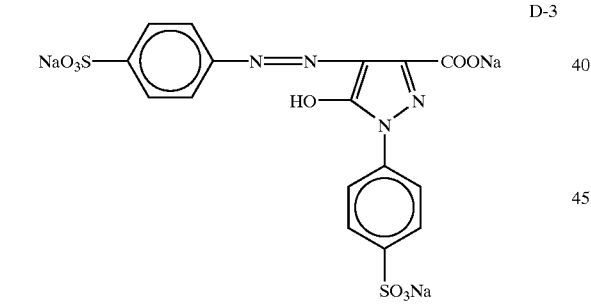
D-4
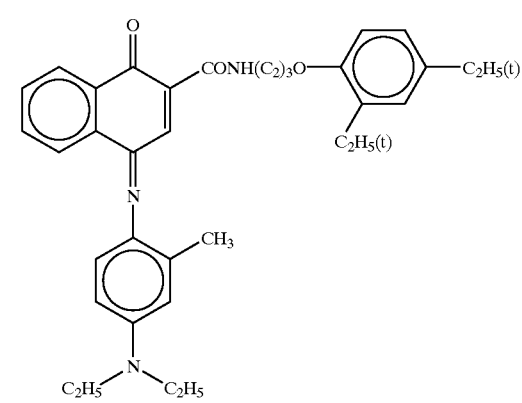
D-5
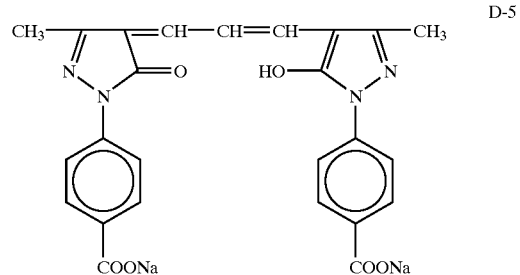
D-6
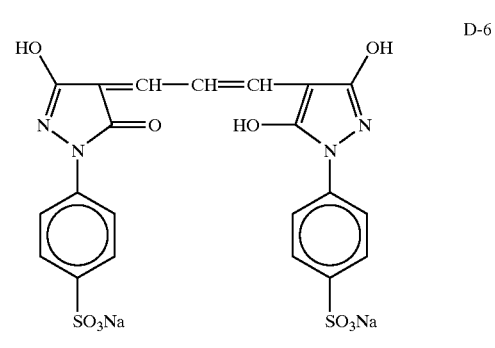
D-7
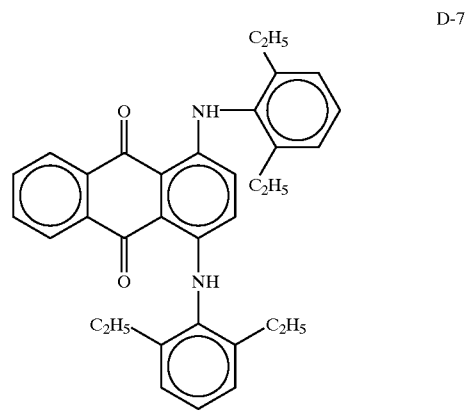
D-8
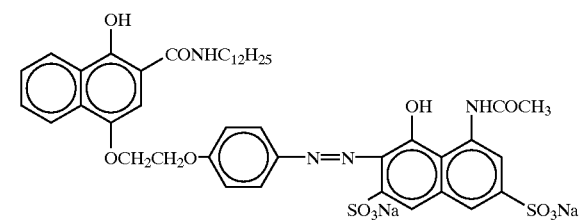
D-9
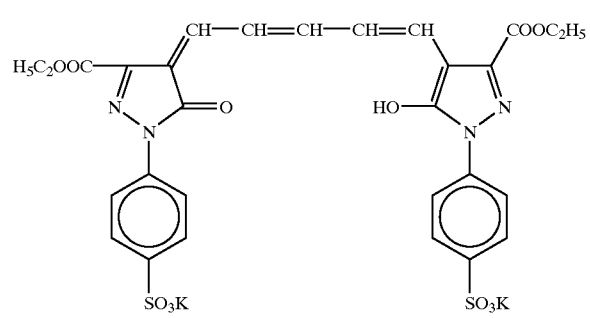

-continued
E-1
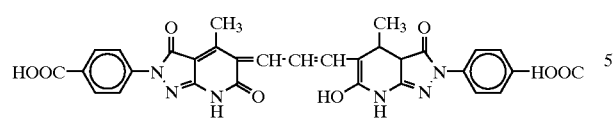
E-2
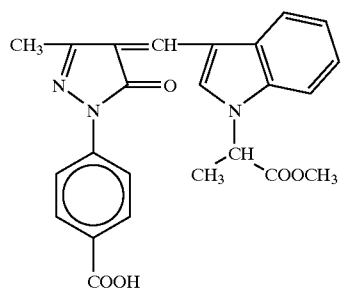
H-1
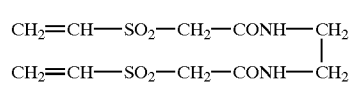
W-1
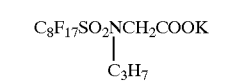
W-2
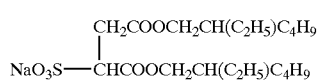
W-3
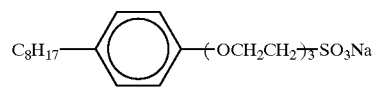
W-4
$C_8H_{17}$—⟨phenyl⟩—$(OCH_2CH_2)_3SO_3Na$
W-5
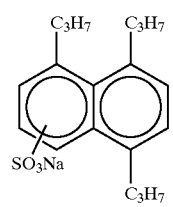
W-6
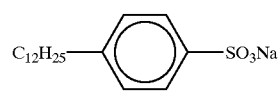
W-7
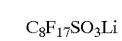
$C_8F_{17}SO_3Li$
-continued
P-1
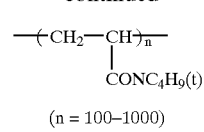
(n = 100–1000)
P-2
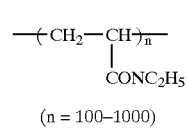
(n = 100–1000)
SO-1
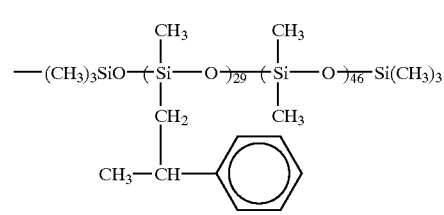
F-1
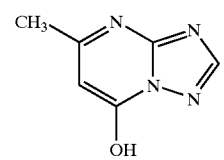
F-2
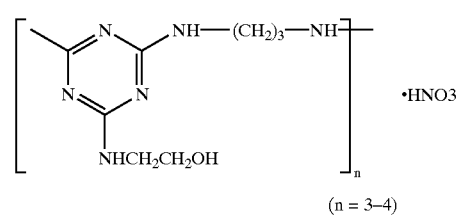
(n = 3–4)
F-3
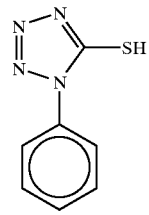
F-4
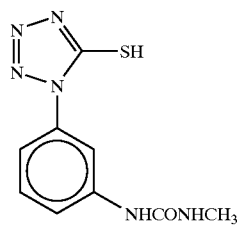
F-5
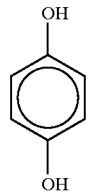

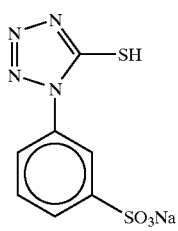

F-6

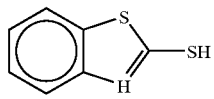

F-7

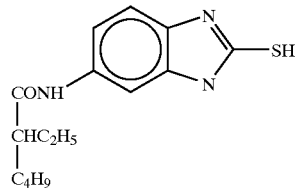

F-8

(Preparation of Dispersions of Organic Solid Disperse Dyes)
(Preparation of Dispersion of Dye E-1)

100 g of Pluronic F88 (an ethylene oxide-propylene oxide block copolymer) manufactured by BASF CORP. and water were added to a wet cake of the dye E-1 (the net weight of E-1 was 270 g), and the resultant material was stirred to make 4,000 g. Next, the Ultra Visco Mill (UVM-2) manufactured by Imex K.K. was filled with 1,700 mL of zirconia beads with an average grain size of 0.5 mm, and the slurry was milled through this UVM-2 at a peripheral speed of approximately 10 m/sec and a discharge rate of 0.5 L/min for 2 hr. The beads were filtered out, and water was added to dilute the material to a dye concentration of 3%. After that, the material was heated to 90° C. for 10 hr for stabilization. The average grain size of the obtained fine dye grains was 0.30 µm, and the grain size distribution (grain size standard deviation×100/average grain size) was 20%.

(Making of Solid Dispersion of Dye E-2)

Water and 270 g of W-4 were added to 1,400 g of a wet cake of E-2 containing 30 mass % of water, and the resultant material was stirred to form a slurry having an E-2 concentration of 40 mass %. Next, the Ultra Visco Mill (UVM-2) manufactured by Imex K.K. was filled with 1,700 mL of zirconia beads with an average grain size of 0.5 mm, and the slurry was milled through this UVM-2 at a peripheral speed of approximately 10 m/sec and a discharge rate of 0.5 L/min for 8 hr, thereby obtaining a solid fine-grain dispersion of E-2. This dispersion was diluted to 20 mass % by ion exchange water to obtain a solid fine-grain dispersion. The average grain size was 0.15 µm.

Samples 102 to 121 were made by replacing the couplers C-4, C-7, and C-8 and the high-boiling organic solvents in the 11th, 12th, and 13th layers of sample 101 with those as shown in Table 6. The couplers were replaced such that couplers of the present invention or comparative couplers were 70% with respect to C-4 and 65% with respect to C-7 and C-8 as a molar ratio.

TABLE 6

| Sample | | Coupler | High-boiling organic solvent (mass ratio to coupler) |
|---|---|---|---|
| 101 | (Comparative example) | As described in text | As described in text |
| 102 | (Comparative example) | Comparative coupler a | Oil-2 (0.3) |
| 103 | (Comparative example) | Comparative coupler b | Oil-2 (0.3) |
| 104 | (Comparative example) | Comparative coupler c | Oil-2 (0.3) |
| 105 | (Comparative example) | Comparative coupler d | Oil-2 (0.3) |
| 106 | (Comparative example) | Comparative coupler e | Oil-2 (0.3) |
| 107 | (Comparative example) | Comparative coupler b | None |
| 108 | (Present invention) | CP-1 | Oil-2 (0.2) |
| 109 | (Present invention) | CP-1 | None |
| 110 | (Present invention) | CP-2 | Oil-2 (0.2) |
| 111 | (Present invention) | CP-3 | Oil-2 (0.2) |
| 112 | (Present invention) | CP-6 | Oil-2 (0.2) |
| 113 | (Present invention) | CP-17 | Oil-2 (0.5) |
| 114 | (Present invention) | CP-18 | Oil-2 (0.2) |
| 115 | (Present invention) | CP-26 | None |
| 116 | (Present invention) | CP-30 | None |
| 117 | (Present invention) | CP-33 | Oil-6 (0.3) |
| 118 | (Present invention) | CP-47 | Oil-2 (0.2) |
| 119 | (Present invention) | CP-54 | Oil-2 (0.2) |
| 120 | (Present invention) | CP-6 | None |
| 121 | (Present invention) | CP-6 | Oil-6 (0.1) |

Comparative coupler a

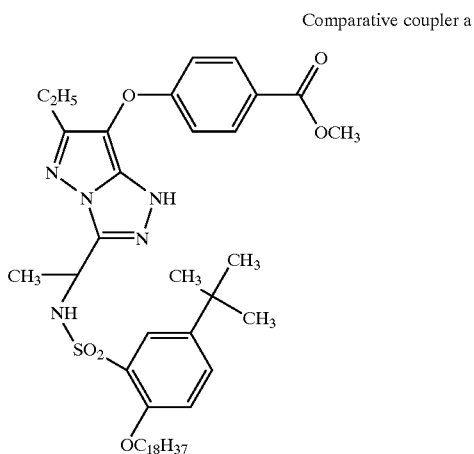

Comparative coupler b

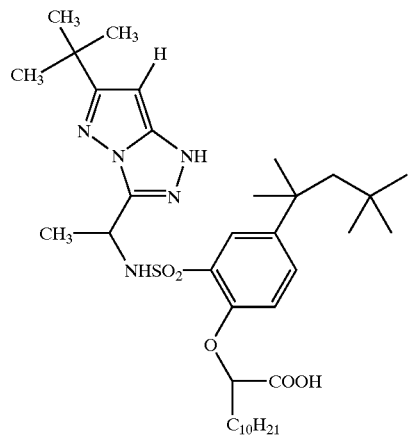

Comparative coupler c

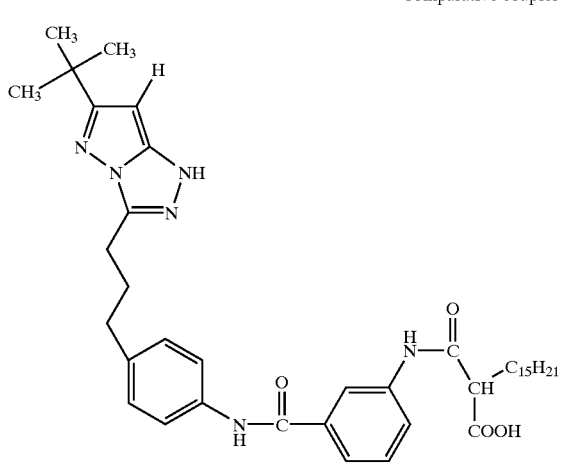

JP-A-1-102557
Exemplified Compound M-2

Comparative coupler d

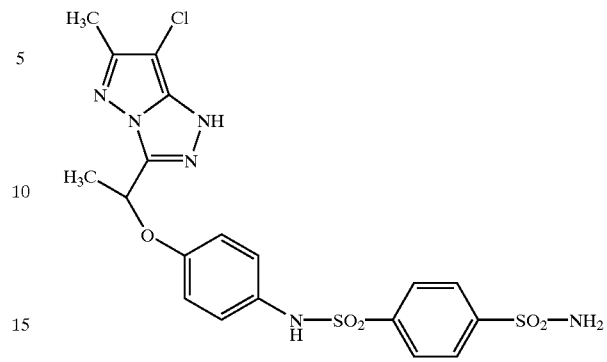

JPA-A-5-150419
Compound (2)

Comparative coupler e

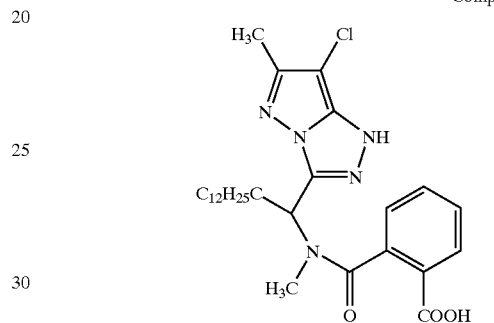

JPA-A-63-291058

In this example, the following development process (development A) was performed.

In this process, unexposed and completely exposed specimens of sample 101 were subjected to running processing, at a ratio of 1:1, until the replenishment volume reached to 4 times the tank volume. After that, processing for evaluation was performed.

| Processing Step | Time | Temperature | Tank volume | Replenishment rate |
|---|---|---|---|---|
| 1st development | 6 min | 38° C. | 37 L | 2,200 mL/m² |
| 1st washing | 2 min | 38° C. | 16 L | 4,000 mL/m² |
| Reversal | 2 min | 33° C. | 17 L | 1,100 mL/m² |
| Color development | 6 min | 38° C. | 30 L | 2,200 mL/m² |
| Pre-bleaching | 2 min | 38° C. | 19 L | 1,100 mL/m² |
| Bleaching | 6 min | 38° C. | 30 L | 220 mL/m² |
| Fixing | 4 min | 38° C. | 29 L | 1,100 mL/m² |
| 2nd washing | 4 min | 38° C. | 35 L | 4,000 mL/m² |
| Final rinsing | 1 min | 25° C. | 19 L | 1,100 mL/m² |

The compositions of the processing solutions were as follows.

| <1st developer> | <Tank solution> | <Replenisher> |
|---|---|---|
| Nitrilo-N,N,N-trimethylene phosphonic acid · pentasodium salt | 1.5 g | 1.5 g |
| Diethylenetriamine pentaacetic acid · pentasodium salt | 2.0 g | 2.0 g |

-continued

| <1st developer> | <Tank solution> | <Replenisher> |
|---|---|---|
| Sodium sulfite | 30 g | 30 g |
| Hydroquinone.potassium monosulfonate | 20 g | 20 g |
| Potassium carbonate | 15 g | 20 g |
| Potassium bicarbonate | 12 g | 15 g |
| 1-phenyl-4-methyl-4-hydroxymethyl-3-pyrazolidone | 2.5 g | 3.0 g |
| Potassium bromide | 2.5 g | 1.4 g |
| Potassium thiocyanate | 1.2 g | 1.2 g |
| Potassium iodide | 2.0 mg | — |
| Diethyleneglycol | 13 g | 15 g |
| Water to make | 1,000 mL | 1,000 mL |
| pH | 9.60 | 9.60 |

The pH was adjusted by sulfuric acid or potassium hydroxide.

| <Reversal solution> | <Tank solution> | <Replenisher> |
|---|---|---|
| Nitrilo-N,N,N-trimethylene phosphonic acid · pentasodium salt | 3.0 g | the same as tank solution |
| Stannous chloride · dihydrate | 1.0 g | the same as tank solution |
| p-aminophenol | 0.1 g | the same as tank solution |
| Sodium hydroxide | 8 g | the same as tank solution |
| Glacial acetic acid | 15 mL | the same as tank solution |
| Water to make | 1,000 mL | the same as tank solution |
| pH | 6.00 | the same as tank solution |

The pH was adjusted by acetic acid or sodium hydroxide.

| <Color developer> | <Tank solution> | <Replenisher> |
|---|---|---|
| Nitrilo-N,N,N-trimethylene phosphonic acid · pentasodium salt | 2.0 g | 2.0 g |
| Sodium sulfite | 6.0 g | 6.0 g |
| Trisodium phosphate · dodecahydrate | 30 g | 30 g |
| Potassium bromide | 1.0 g | — |
| Potassium iodide | 90 mg | — |
| Sodium hydroxide | 12.0 g | 12.0 g |
| Citrazinic acid | 0.7 g | 0.7 g |
| N-ethyl-N-(β-methanesulfonamidoethyl)-3-methyl-4-aminoaniline.3/2 sulfuric acid.monohydrate | 7.0 g | 7.5 g |
| 3,6-dithiaoctane-1,8-diol | 1.0 g | 1.0 g |
| Water to make | 1,000 mL | 1,000 mL |
| pH | 11.90 | 12.05 |

The pH was adjusted by sulfuric acid or potassium hydroxide.

| <Pre-bleaching solution> | <Tank solution> | <Replenisher> |
|---|---|---|
| Ethylenediaminetetraacetic acid ·disodium salt · dihydrate | 8.0 g | 8.0 g |
| Sodium sulfite | 4.0 g | 5.0 g |
| 1-thioglycerol | 0.4 g | 0.4 g |
| Formaldehyde sodium bisulfite adduct | 35 g | 40 g |
| Water to make | 1,000 mL | 1,000 mL |
| pH | 6.30 | 6.10 |

The pH was adjusted by acetic acid or sodium hydroxide.

| <Bleaching solution> | <Tank solution> | <Replenisher> |
|---|---|---|
| Ethylenediaminetetraacetic acid · disodium · salt · dihydrate | 2.0 g | 4.0 g |
| Ethylenediaminetetraacetic acid · Fe(III) · ammonium · dihydrate | 120 g | 240 g |
| Potassium bromide | 100 g | 200 g |
| Ammonium nitrate | 10 g | 20 g |
| Water to make | 1,000 mL | 1,000 mL |
| pH | 5.70 | 5.50 |

The pH was adjusted by nitric acid or sodium hydroxide.

| <Fixing solution> | <Tank solution> | <Replenisher> |
|---|---|---|
| Ammonium thiosulfate | 80 g | the same as tank solution |
| Sodium sulfite | 5.0 g | the same as tank solution |
| Sodium bisulfite | 5.0 g | the same as tank solution |
| Water to make | 1,000 mL | the same as tank solution |
| pH | 6.60 | the same as tank solution |

The pH was adjusted by acetic acid or ammonia water.

| <Stabilizer> | <Tank solution> | <Replenisher> |
|---|---|---|
| 1,2-benzoisothiazoline-3-one | 0.02 g | 0.03 g |
| Polyoxyethylene-p-mononyl phenylether (average polymerization degree = 10) | 0.3 g | 0.3 g |
| Polymaleic acid (average molecular weight = 2,000) | 0.1 g | 0.15 g |
| Water to make | 1,000 mL | 1,000 mL |
| pH | 7.0 | 7.0 |

In the above development process, the solution was continuously circulated and stirred in each bath. In addition, a blowing pipe having small holes (0.3 mm in diameter) formed at intervals of 1 cm was attached to the lower surface of each tank to continuously blow nitrogen gas and stir the solution.

(Evaluation of Samples)
(Evaluation of Color Forming Efficiency)

Samples 101 to 121 were cut into the form of strips and exposed to white light at a color temperature of 4,800° K via a wedge having a continuously changing density. Each resultant sample was subjected to development (development A) described above, and the density of the sample was measured. The maximum magenta density (status A) measured was taken as a characteristic value, and the results are shown in Table 7. The larger the numerical value, the higher the color forming efficiency.

(Evaluation of Yellow Coloration on White Ground)

Samples 101 to 121 were cut into the form of strips, exposed for 1 sec in the open air in the daytime, and subjected to development (development A), thereby making entirely white samples.

These samples were stored in an atmosphere of 60° C. and 40% in a dark place for 15 days. Each resultant sample was irradiated with light from its back side for 2 days by using a xenon light fadeometer having an illuminance of 80,000 lux, and a change in the yellow density on the white ground during the period of irradiation with light was observed. A rise width of the yellow density (status A) caused by the irradiation with light is shown as a characteristic value in Table 7.

TABLE 7

Results of evaluation

| Sample | | Maximum magenta density | Yellow coloration on white (irradiation with light after storage in dark place) |
|---|---|---|---|
| 101 | (Comparative example) | 3.00 | 0.04 |
| 102 | (Comparative example) | 2.40 | 0.01 |
| 103 | (Comparative example) | 3.50 | 0.15 |
| 104 | (Comparative example) | 3.00 | 0.20 |
| 105 | (Comparative example) | 1.20 | 0.15 |
| 106 | (Comparative example) | 3.10 | 0.13 |
| 107 | (Comparative example) | 3.40 | 0.10 |
| 108 | (Present invention) | 3.40 | 0.03 |
| 109 | (Present invention) | 3.40 | 0.02 |
| 110 | (Present invention) | 3.25 | 0.02 |
| 111 | (Present invention) | 3.30 | 0.01 |
| 112 | (Present invention) | 3.45 | 0 |
| 113 | (Present invention) | 3.20 | 0 |
| 114 | (Present invention) | 3.50 | 0 |
| 115 | (Present invention) | 3.45 | 0.02 |
| 116 | (Present invention) | 3.40 | 0.01 |
| 117 | (Present invention) | 3.20 | 0.02 |
| 118 | (Present invention) | 3.20 | 0 |
| 119 | (Present invention) | 3.20 | 0.01 |
| 120 | (Present invention) | 3.40 | 0 |
| 121 | (Present invention) | 3.35 | 0 |

As shown by the results in Table 7, a coupler a (sample 102) generated stains little but had insufficient color forming efficiency. On the other hand, couplers b, c, d, and e (samples 103 to 107) undesirably generated large amounts of stains.

In contrast, each of samples 108 to 121 using couplers of the present invention had high color forming efficiency and colored the white ground only slightly. In particular, compounds having a substituent with 4 or more carbon atoms in a phenyl group of a phenylsulfonylamino group, which was the one further from a pyrazolotriazole nucleus, caused little yellow coloration. Examples are CP-2, CP-3, CP-6, CP-17, CP-18, CP-30, CP-47, and CP-54.

EXAMPLE 2

(Making of Sample 201)

A color lightsensitive material including two layers having the following compositions was coated on a 127-μm thick undercoated cellulose triacetate film support, thereby making sample 201. The numbers represent the addition amounts per m². The amount of a silver halide is indicated by a silver amount.

| 1st layer: Silver halide emulsion layer | |
|---|---|
| Silver iodobromide monodisperse tabular grain silver | 1.20 g |
| average equivalent-sphere grain size | 0.3 μm |
| variation coefficient | 18% |
| AgI content | 4.0 mol% |
| Gelatin | 3.50 g |
| Coupler C-8 | 0.45 g |
| High-boiling organic solvent Oil-2 | 0.23 g |
| 2nd layer: Protective layer | |
| Gelatin | 2.00 g |
| polymethylmethacrylate | 0.10 g |
| (average grain size 2.0 μm) | |
| Surfactant W-1 | 0.15 g |
| Gelatin hardener H-1 | 0.17 g |

(Making of samples 201–212)

Samples 202 to 212 were made following the same procedures as for sample 201 except that the magenta coupler in the first layer of sample 201 was replaced with those as shown in Table 8. Since the molar absorption coefficient of a pyrazolotriazole-based coupler is higher than that of a pyrazolone-based coupler, the addition amount was set to 0.6-fold mols with respect to the coupler C-8.

TABLE 8

Configuration of sample

| Sample | | Coupler | Amount of high-boiling organic solvent Oil-1 (mass ratio to coupler) |
|---|---|---|---|
| 201 | (Comparative example) | C-8 | 0.4 |
| 202 | (Comparative example) | C-8 | None |
| 203 | (Comparative example) | Comparative coupler a | 0.5 |
| 204 | (Comparative example) | Comparative coupler a | None |
| 205 | (Comparative example) | Comparative coupler b | 0.5 |
| 206 | (Comparative example) | Comparative coupler b | None |
| 207 | (Present invention) | CP-3 | 0.5 |
| 208 | (Present invention) | CP-3 | None |
| 209 | (Present invention) | CP-5 | 0.5 |
| 210 | (Present invention) | CP-5 | None |
| 211 | (Present invention) | CP-1 | 0.5 |
| 212 | (Present invention) | CP-1 | None |

Evaluation of dependence on addition amount of color developing agent: The same processing as development (development A) was performed except that the amounts of a color developing agent [N-ethyl-N(β-methanesulfonamidoethyl) -3-methyl-4-amino aniline·3/2 sulfuric acid·monohydrate] in a color developer were 2.0 and 11.0 g per liter. The magenta density in processing in which the amount of the color developing agent was 2.0 g/L was measured with the same exposure amount as giving a magenta density of 1.0 in processing in which the amount was 11.0 g/L. This magenta density was used in the following equation.

(1.0−density in processing of color developing agent 2.0 g/L)× 100=change rate (%)

The smaller the change rate, the smaller the color density change by variations of the color developing agent.

Evaluation of hue: uniform exposure was given such that the density was 1.0, and development A described above was performed. Each resultant sample was measured with a spectrophotometer to read the wavelength of λmax and the values at 500 and 600 nm when λmax was 1.0.

The wavelength of ;max is preferably near 550 nm to which the eye is most sensitive. Also, the smaller the values at 500 and 600 nm, the smaller the side absorption and the more favorable the hue.

The above results are shown in Table 9.

TABLE 9

| | Results of evaluation | | | |
|---|---|---|---|---|
| Sample | λ max (nm) Preferably near 550 | Absorption (ratio) at 500 nm Preferably 0.45 or less | Absorption (ratio) at 600 nm Preferably 0.25 or less | Dependence (%) of color density on developing agent amount Preferably as large as possible |
| 201 (Comparative example) | 551 | 0.46 | 0.41 | 78 |
| 202 (Comparative example) | 552 | 0.45 | 0.44 | 75 |
| 203 (Comparative example) | 549 | 0.45 | 0.23 | 60 |
| 204 (Comparative example) | 551 | 0.47 | 0.28 | 33 |
| 205 (Comparative example) | 558 | 0.40 | 0.40 | 90 |
| 206 (Comparative example) | 558 | 0.40 | 0.40 | 84 |
| 207 (Present invention) | 549 | 0.43 | 0.22 | 85 |
| 208 (Present invention) | 551 | 0.43 | 0.24 | 80 |
| 209 (Present invention) | 551 | 0.39 | 0.19 | 80 |
| 210 (Present invention) | 552 | 0.41 | 0.23 | 72 |
| 211 (Present invention) | 552 | 0.40 | 0.24 | 90 |
| 212 (Present invention) | 552 | 0.40 | 0.26 | 88 |

Samples 201 and 202 using the conventional pyrazolone magenta coupler substantially satisfied the dependence on the addition amount of color developing agent. However, these samples caused large absorption at 600 nm in hue, and this is unpreferable in color reproduction. Any of samples 203 to 206 using the comparative couplers did not satisfy both the dependence on the addition amount of color developing agent and the hue. By contrast, any of samples 207 to 212 using the couplers of the present invention obviously had small dependence on the addition amount of color developing agent and good hue.

A coupler of the present invention is a novel pyrazolotriazole-based compound which can be manufactured at low cost, has high manufacturing suitability, and achieves high color forming efficiency even when the use amount of a high-boiling organic solvent is reduced. Also, a silver halide color photographic lightsensitive material of the present invention has high color reproducibility and high image stability, and hardly produces stains. This lightsensitive material lowers the sensitivity little when stored, and changes the photographic properties little by variations in processing compositions.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A silver halide color photographic lightsensitive material comprising at least one photosensitive silver halide emulsion layer on a support, wherein the emulsion layer contains a magenta coupler represented by formula (M-1) below (M-1)

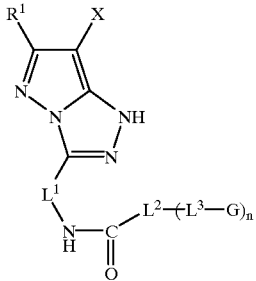

wherein $R^1$ represents a substituted or nonsubstituted alkyl group;

each of $L^1$ and $L^2$ independently represents a substituted or nonsubstituted alkylene group, or substituted or nonsubstituted arylene group;

in —$L^3$—G, $L^3$ represents —NH—$SO_2$—whose left side bonds to NH—CO—$L^2$ and whose right side bonds to G, and G represents a substituted or nonsubstituted alkyl group or substituted or nonsubstituted aryl group, X represents a hydrogen atom or a group which splits off when coupling with an oxidized form of a developing agent;

n represents 1 or 2, when $L^2$ is an alkylene group, or n represents an integer from 1 to 5, when $L^2$ is an arylene group; and a plurality of —$L^3$—G's can be the same or different, when n is 2 or more.

2. A silver halide color photographic lightsensitive material comprising at least one photosensitive silver halide emulsion layer on a support, wherein the emulsion layer contains a magenta coupler represented by formula (M-2) below:

(M-2)

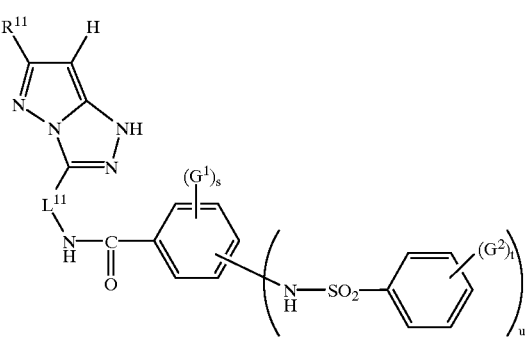

wherein $R^{11}$ represents a 1- to 6-carbon nonsubstituted alkyl group;

$L^{11}$ represents a 1- to 6-carbon nonsubstituted alkylene group;

each of G¹ and G² independently represents a substituted or nonsubstituted alkyl group, substituted or nonsubstituted alkoxy group, substituted or nonsubstituted aryloxy group, halogen atom, substituted or nonsubstituted acylamino group, substituted or nonsubstituted alkoxycarbonyl group, or substituted or nonsubstituted aminocarbonyl group;

s represents an integer from 0 to 4;

t represents an integer from 0 to 5;

u represents 1 to 2;

the sum of s an u does not exceed 5; and the value of pKa of —NHSO$_2$— between the two phenyl groups at 25° in a solution of THF/H$_2$O=6/4 is 12 or less.

3. The silver halide color photographic lightsensitive material according to claim 2, wherein the magenta coupler is represented by formula (M-3) below:

(M-3)

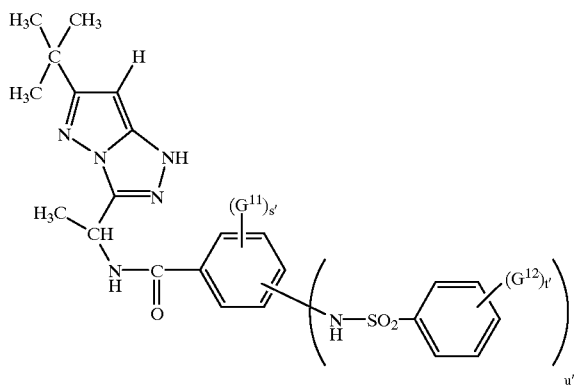

wherein each of G¹¹ and G¹² independently represents a 1- to 30-carbon, substituted or nonsubstituted alkyl group, 1- to 30-carbon, substituted or nonsubstituted alkoxy group, 6- to 30-carbon, substituted or nonsubstituted aryloxy group, halogen atom, 1- to 30-carbon, substituted or nonsubstituted acylamino group, 2- to 30-carbon, substituted or nonsubstituted alkoxycarbonyl group, or 1- to 30-carbon, substituted or nonsubstituted aminocarbonyl group;

s' represents an integer from 0 to 4;

t' represents an integer from 0 to 5;

u' represents 1 or 2; and the sum of s' and u' does not exceed 5.

4. A silver halide color photographic lightsensitive material comprising at least one photosensitive silver halide emulsion layer on a support, wherein the emulsion layer contains a magenta coupler represented by formula (M-1) below:

(M-1)

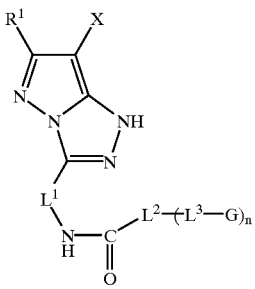

wherein each substituent of the formula (M-1) is as follows:

R¹ is a 1- to 10-carbon, straight-chain, branched, or cyclic, nonsubstituted alkyl group;

L¹ is a 1- to 10-carbon, nonsubstituted alkylene group;

L² is a 6- to 30-carbon, substituted or nonsubstituted arylene group;

L³ is —NH—SO$_2$— (the left side bonds to NH—CO—L² and the right side bonds to G);

n is 1 or 2;

X is a hydrogen atom, halogen atom, 6- to 30-carbon arylthio group, or 6- to 30-carbon aryloxy group; and G is a 6- to 30-carbon, substituted or nonsubstituted aryl group.

5. The silver halide color photographic lightsensitive material according to claim 1, which is a color reversal photographic lightsensitive material.

6. The silver halide color photographic lightsensitive material according to claim 2, which is a color reversal photographic lightsensitive material.

7. The silver halide color photographic lightsensitive material according to claim 3, which is a color reversal photographic lightsensitive material.

8. The silver halide color photographic lightsensitive material according to claim 4, which is a color reversal photographic lightsensitive material.

9. The silver halide color photographic lightsensitive material of claim 1, wherein R¹ represents a 1–30 carbon, substituted or nonsubstituted alkyl group.

10. The silver halide color photographic lightsensitive material of claim 1, wherein L¹ or L² represents a 1–30 carbon, substituted or nonsubstituted alkylene group which is straight-chain, branched or cyclic.

11. The silver halide color photographic lightsensitive material of claim 1, wherein L¹ represents a 6–35 carbon, substituted or nonsubstituted arylene group or L² represents a 6–40 carbon, substituted or nonsubstituted arylene group.

12. The silver halide color photographic lightsensitive material of claim 1, wherein G represents a 1–30 carbon, substituted or nonsubstituted alkyl group or a 6–30 carbon, substituted or nonsubstituted aryl group.

13. The silver halide color photographic lightsensitive material of claim 1, wherein said magenta coupler has a pKa value of 12 or less.

14. The silver halide color photographic lightsensitive material of claim 1, wherein said magenta coupler is not formed into a composition with oil.

15. The silver halide color photographic lightsensitive material of claim 1, wherein said magenta coupler is present in the material in an amount of 0.01 to 10 g per m².

16. The silver halide color photographic lightsensitive material of claim 2, wherein said magenta coupler is present in the material in an amount of 0.01 to 10 g per m².

17. The silver halide color photographic lightsensitive material of claim 4, wherein said magenta coupler is present in the material in an amount of 0.01 to 10 g per m².

18. The silver halide color photographic lightsensitive material of claim 1, wherein said magenta coupler is present in the material in an amount of 1×10⁻³ to 1 mol per mol of silver halide in the same photosensitive layer.

19. The silver halide color photographic lightsensitive material of claim 2, wherein said magenta coupler is present in the material in an amount of 1×10⁻³ to 1 mol per mol of silver halide in the same photosensitive layer.

* * * * *